(12) United States Patent
Kim et al.

(10) Patent No.: US 7,740,839 B2
(45) Date of Patent: Jun. 22, 2010

(54) EC SOD AND CELL TRANSDUCING EC SOD AND USE THEREOF

(75) Inventors: Tae-Yoon Kim, Asia Seonsoochon Apt. #8-702, Jamsil-dong, Songpa-gu, Seoul (KR) 138-220; Bo-Yeun Choung, Seoul (KR)

(73) Assignees: Tae-Yoon Kim, Seoul (KR); Bio Clue & Solution Co., Ltd., Seoul (KR)

( * ) Notice: Subject to any disclaimer, the term of this patent is extended or adjusted under 35 U.S.C. 154(b) by 411 days.

(21) Appl. No.: 10/577,775

(22) PCT Filed: Oct. 29, 2004

(86) PCT No.: PCT/KR2004/002757

§ 371 (c)(1),
(2), (4) Date: Apr. 28, 2006

(87) PCT Pub. No.: WO2005/042583

PCT Pub. Date: May 12, 2005

(65) Prior Publication Data

US 2008/0069808 A1    Mar. 20, 2008

(30) Foreign Application Priority Data

Oct. 31, 2003    (KR) ...................... 10-2003-0076629

(51) Int. Cl.
*A61K 38/44*    (2006.01)
(52) U.S. Cl. .................................... 424/94.4
(58) Field of Classification Search ................ 424/94.4; 435/25
See application file for complete search history.

(56) References Cited

U.S. PATENT DOCUMENTS

| 5,366,729 A | 11/1994 | Marklund et al. |
| 5,464,614 A | 11/1995 | Meyer |
| 6,011,067 A * | 1/2000 | Hersh .......................... 514/562 |

FOREIGN PATENT DOCUMENTS

WO    96/40223    * 12/1996

OTHER PUBLICATIONS

Choung et al., Journal of Investigative Dermatology, 122(3), pp. A143, 2004.*
Sasaki et al., "Effects of a Single Exposure to UVB Radiation on the Activities and Protein Levels of Copper-Zinc and Manganese Superoxide Dismutase in Cultured Human Keratinocytes," *Photochemistry and Photobiology*, 1997, vol. 64, No. 4, pp. 707-713, The American Society for Photobiology, Lawrence, Kansas, U.S.A.
Takahashi et al., "Copper, zinc-superoside dismutase protects from ultraviolet B-induced apoptosis of SV40-transformed human keratinocytes: the protection is associated with the increased levels of antioxidant enzymes," *Journal of Dermatological Science*, 2000, vol. 23, pp. 21-21, Elsevier Science Ireland, Ltd., Ireland.
Park et al., "9-Polylysine Protein Transduction Domain: Enhanced Penetration Efficiency of Superoxide Dismutase into Mammalian Cells and Skin," *Molecules and Cells*, 2002, vol. 12, No. 2, pp. 202-208, Korean Society for Molecular Biology, Republic of Korea.

* cited by examiner

*Primary Examiner*—Maryam Monshipouri
(74) *Attorney, Agent, or Firm*—Buchanan Ingersoll & Rooney PC

(57) ABSTRACT

The present invention relates to an EC SOD, a cell-transducing EC SOLD, and the use thereof. More particularly, the present invention relates to an EC SOD, an EC SOD fusion protein enhanced Cell-transduction ability, and the use thereof for preventing or treating skin diseases.

1 Claim, 27 Drawing Sheets

A

B

_US 7,740,839 B2_

SEQUENCE LISTING

<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
atgttggcct tcttgttc                                                 18

```
<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
ttaagtggtc ttgcactc                                                 18

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
agtctcgaga tgttggcctt cttgttctac ggc                                33

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
gatcctcgag tggtcttgca ctcgctct                                      28

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
atctctagaa tgctggcgct actgtgt                                       27

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
atcgaatcct caggcggcct tgcactcgct ctct                               34

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gatcctcgag tggacgggcg aggactcggc                                    30

<210> SEQ ID NO 8
<211> LENGTH: 31
<212> TYPE: DNA
<213> ORGANISM: Artificial Sequence
<220> FEATURE:
<223> OTHER INFORMATION: primer
```

<210> SEQ ID NO 8

<400> SEQUENCE: 8
gatcctcgag tcaggcggcc ttgcactcgc t    31

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gatcctcgag tggacgggcg aggactcggc    30

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
aatgctcgag tcactctgag tgctcccgcg c    31

<210> SEQ ID NO 11
<211> LENGTH: 240
<212> TYPE: PRT
<213> ORGANISM: Homo sapiens
<220> FEATURE:
<221> NAME/KEY: PEPTIDE
<222> LOCATION: (1)..(240)
<223> OTHER INFORMATION: Human EC SOD

<400> SEQUENCE: 11

```
Met Leu Ala Leu Leu Cys Ser Cys Leu Leu Leu Ala Ala Gly Ala Ser
 1               5                  10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
        35                  40                  45

Val Met Gln Arg Arg Asp Asp Gly Thr Leu His Ala Ala Cys Gln
    50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Ser Arg Ala
            100                 105                 110

Ile His Val His Gln Phe Gly Asp Leu Ser Gln Gly Cys Glu Ser Thr
        115                 120                 125

Gly Pro His Tyr Asn Pro Leu Ala Val Pro His Pro Gln His Pro Gly
    130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175

Ala Val Val Val His Ala Gly Glu Asp Asp Leu Gly Arg Gly Gly Asn
            180                 185                 190

Gln Ala Ser Val Glu Asn Gly Asn Ala Gly Arg Arg Leu Ala Cys Cys
        195                 200                 205
```

```
Val Val Gly Val Cys Gly Pro Gly Leu Trp Glu Arg Gln Ala Arg Glu
    210                 215                 220

His Ser Glu Arg Lys Lys Arg Arg Arg Glu Ser Glu Cys Lys Ala Ala
225                 230                 235                 240
```

<210> SEQ ID NO 12
<211> LENGTH: 231
<212> TYPE: PRT
<213> ORGANISM: Artificial Sequence
<220> FEATURE:
<223> OTHER INFORMATION: TAT-EC SOD fusion protein

<400> SEQUENCE: 12

```
Arg Lys Lys Arg Arg Gln Arg Arg Trp Thr Gly Glu Asp Ser Ala
  1               5                  10                  15

Glu Pro Asn Ser Asp Ser Ala Glu Trp Ile Arg Asp Met Tyr Ala Lys
               20                  25                  30

Val Thr Glu Ile Trp Gln Glu Val Met Gln Arg Arg Asp Asp Asp Gly
             35                  40                  45

Thr Leu His Ala Ala Cys Gln Val Gln Pro Ser Ala Thr Leu Asp Ala
 50                  55                  60

Ala Gln Pro Arg Val Thr Gly Val Val Leu Phe Arg Gln Leu Ala Pro
 65                  70                  75                  80

Arg Ala Lys Leu Asp Ala Phe Phe Ala Leu Glu Gly Phe Pro Thr Glu
                 85                  90                  95

Pro Asn Ser Ser Ser Arg Ala Ile His Val His Gln Phe Gly Asp Leu
                100                 105                 110

Ser Gln Gly Cys Glu Ser Thr Gly Pro His Tyr Asn Pro Leu Ala Val
            115                 120                 125

Pro His Pro Gln His Pro Gly Asp Phe Gly Asn Phe Ala Val Arg Asp
130                 135                 140

Gly Ser Leu Trp Arg Tyr Arg Ala Gly Leu Ala Ala Ser Leu Ala Gly
145                 150                 155                 160

Pro His Ser Ile Val Gly Arg Ala Val Val His Ala Gly Glu Asp
                165                 170                 175

Asp Leu Gly Arg Gly Gly Asn Gln Ala Ser Val Glu Asn Gly Asn Ala
                180                 185                 190

Gly Arg Arg Leu Ala Cys Cys Val Val Gly Val Cys Gly Pro Gly Leu
            195                 200                 205

Trp Glu Arg Gln Ala Arg Glu His Ser Glu Arg Lys Lys Arg Arg Arg
210                 215                 220

Glu Ser Glu Cys Lys Ala Ala
225                 230
```

<210> SEQ ID NO 13
<211> LENGTH: 218
<212> TYPE: PRT
<213> ORGANISM: Artificial Sequence
<220> FEATURE:
<223> OTHER INFORMATION: TAT-delta HD/EC SOD fusion protein

<400> SEQUENCE: 13

```
Arg Lys Lys Arg Arg Gln Arg Arg Trp Thr Gly Glu Asp Ser Ala
  1               5                  10                  15

Glu Pro Asn Ser Asp Ser Ala Glu Trp Ile Arg Asp Met Tyr Ala Lys
               20                  25                  30

Val Thr Glu Ile Trp Gln Glu Val Met Gln Arg Arg Asp Asp Asp Gly
             35                  40                  45
```

```
Thr Leu His Ala Ala Cys Gln Val Gln Pro Ser Ala Thr Leu Asp Ala
 50                  55                  60

Ala Gln Pro Arg Val Thr Gly Val Val Leu Phe Arg Gln Leu Ala Pro
 65                  70                  75                  80

Arg Ala Lys Leu Asp Ala Phe Phe Ala Leu Glu Gly Phe Pro Thr Glu
                 85                  90                  95

Pro Asn Ser Ser Arg Ala Ile His Val His Gln Phe Gly Asp Leu
                100                 105                 110

Ser Gln Gly Cys Glu Ser Thr Gly Pro His Tyr Asn Pro Leu Ala Val
            115                 120                 125

Pro His Pro Gln His Pro Gly Asp Phe Gly Asn Phe Ala Val Arg Asp
        130                 135                 140

Gly Ser Leu Trp Arg Tyr Arg Ala Gly Leu Ala Ala Ser Leu Ala Gly
145                 150                 155                 160

Pro His Ser Ile Val Gly Arg Ala Val Val His Ala Gly Glu Asp
                165                 170                 175

Asp Leu Gly Arg Gly Gly Asn Gln Ala Ser Val Glu Asn Gly Asn Ala
                180                 185                 190

Gly Arg Arg Leu Ala Cys Cys Val Val Gly Val Cys Gly Pro Gly Leu
            195                 200                 205

Trp Glu Arg Gln Ala Arg Glu His Ser Glu
        210                 215

<210> SEQ ID NO 14
<211> LENGTH: 231
<212> TYPE: PRT
<213> ORGANISM: Artificial Sequence
<220> FEATURE:
<223> OTHER INFORMATION: R9-EC SOD fusion protein

<400> SEQUENCE: 14

Arg Arg Arg Arg Arg Arg Arg Arg Arg Trp Thr Gly Glu Asp Ser Ala
 1               5                  10                  15

Glu Pro Asn Ser Asp Ser Ala Glu Trp Ile Arg Asp Met Tyr Ala Lys
                 20                  25                  30

Val Thr Glu Ile Trp Gln Glu Val Met Gln Arg Arg Asp Asp Asp Gly
             35                  40                  45

Thr Leu His Ala Ala Cys Gln Val Gln Pro Ser Ala Thr Leu Asp Ala
 50                  55                  60

Ala Gln Pro Arg Val Thr Gly Val Val Leu Phe Arg Gln Leu Ala Pro
 65                  70                  75                  80

Arg Ala Lys Leu Asp Ala Phe Phe Ala Leu Glu Gly Phe Pro Thr Glu
                 85                  90                  95

Pro Asn Ser Ser Arg Ala Ile His Val His Gln Phe Gly Asp Leu
                100                 105                 110

Ser Gln Gly Cys Glu Ser Thr Gly Pro His Tyr Asn Pro Leu Ala Val
            115                 120                 125

Pro His Pro Gln His Pro Gly Asp Phe Gly Asn Phe Ala Val Arg Asp
        130                 135                 140

Gly Ser Leu Trp Arg Tyr Arg Ala Gly Leu Ala Ala Ser Leu Ala Gly
145                 150                 155                 160

Pro His Ser Ile Val Gly Arg Ala Val Val His Ala Gly Glu Asp
                165                 170                 175

Asp Leu Gly Arg Gly Gly Asn Gln Ala Ser Val Glu Asn Gly Asn Ala
                180                 185                 190
```

Gly Arg Arg Leu Ala Cys Cys Val Val Gly Val Cys Gly Pro Gly Leu
            195                 200                 205

Trp Glu Arg Gln Ala Arg Glu His Ser Glu Arg Lys Lys Arg Arg
        210                 215                 220

Glu Ser Glu Cys Lys Ala Ala
225                 230

<210> SEQ ID NO 15
<211> LENGTH: 232
<212> TYPE: PRT
<213> ORGANISM: Artificial Sequence
<220> FEATURE:
<223> OTHER INFORMATION: K10-EC SOD fusion protein

<400> SEQUENCE: 15

Lys Lys Lys Lys Lys Lys Lys Lys Lys Trp Thr Gly Glu Asp Ser
1               5                   10                  15

Ala Glu Pro Asn Ser Asp Ser Ala Glu Trp Ile Arg Asp Met Tyr Ala
            20                  25                  30

Lys Val Thr Glu Ile Trp Gln Glu Val Met Gln Arg Arg Asp Asp Asp
        35                  40                  45

Gly Thr Leu His Ala Ala Cys Gln Val Gln Pro Ser Ala Thr Leu Asp
    50                  55                  60

Ala Ala Gln Pro Arg Val Thr Gly Val Val Leu Phe Arg Gln Leu Ala
65                  70                  75                  80

Pro Arg Ala Lys Leu Asp Ala Phe Phe Ala Leu Glu Gly Phe Pro Thr
                85                  90                  95

Glu Pro Asn Ser Ser Ser Arg Ala Ile His Val His Gln Phe Gly Asp
            100                 105                 110

Leu Ser Gln Gly Cys Glu Ser Thr Gly Pro His Tyr Asn Pro Leu Ala
        115                 120                 125

Val Pro His Pro Gln His Pro Gly Asp Phe Gly Asn Phe Ala Val Arg
    130                 135                 140

Asp Gly Ser Leu Trp Arg Tyr Arg Ala Gly Leu Ala Ala Ser Leu Ala
145                 150                 155                 160

Gly Pro His Ser Ile Val Gly Arg Ala Val Val Val His Ala Gly Glu
                165                 170                 175

Asp Asp Leu Gly Arg Gly Gly Asn Gln Ala Ser Val Glu Asn Gly Asn
            180                 185                 190

Ala Gly Arg Arg Leu Ala Cys Cys Val Val Gly Val Cys Gly Pro Gly
        195                 200                 205

Leu Trp Glu Arg Gln Ala Arg Glu His Ser Glu Arg Lys Lys Arg Arg
    210                 215                 220

Arg Glu Ser Glu Cys Lys Ala Ala
225                 230

<210> SEQ ID NO 16
<211> LENGTH: 696
<212> TYPE: DNA
<213> ORGANISM: Artificial Sequence
<220> FEATURE:
<223> OTHER INFORMATION: nucloetide sequence encoding TAT-EC SOD fusion
      protein

<400> SEQUENCE: 16
aggaagaagc ggagacagcg acgaagatgg acgggcgagg actcggcgga gcccaactct      60
gactcggcgg agtggatccg agacatgtac gccaaggtca cggagatctg gcaggaggtc     120

```
atgcagcggc gggacgacga cggcacgctc cacgccgcct gccaggtgca gccgtcggcc    180
acgctggacg ccgcgcagcc ccgggtgacc ggcgtcgtcc tcttccggca gcttgcgccc    240
cgcgccaagc tcgacgcctt cttcgccctg gagggcttcc cgaccgagcc gaacagctcc    300
agccgcgcca tccacgtgca ccagttcggg gacctgagcc agggctgcga gtccaccggg    360
ccccactaca acccgctggc cgtgccgcac ccgcagcacc cgggcgactt cggcaacttc    420
gcggtccgcg acggcagcct ctggaggtac gcgccggcc tggccgcctc gctcgcgggc    480
ccgcactcca tcgtgggccg ggccgtggtc gtccacgctg gcgaggacga cctgggccgc    540
ggcggcaacc aggccagcgt ggagaacggg aacgcgggcc ggcggctggc ctgctgcgtg    600
gtgggcgtgt gcgggcccgg gctctgggag cgccaggcgc gggagcactc agagcgcaag    660
aagcggcggc gcgagagcga gtgcaaggcc gcctga                            696
```

<210> SEQ ID NO 17
<211> LENGTH: 657
<212> TYPE: DNA
<213> ORGANISM: Artificial Sequence
<220> FEATURE:
<223> OTHER INFORMATION: nucleotide sequence encoding TAT-delta HD/EC
    SOD fusion protein

<400> SEQUENCE: 17

```
aggaagaagc ggagacagcg acgaagatgg acgggcgagg actcggcgga gcccaactct     60
gactcggcgg agtggatccg agacatgtac gccaaggtca cggagatctg caggaggtc    120 atgcagcggc gggacgacga cggcacgctc cacgccgcct gccaggtgca gccgtcggcc    180
acgctggacg ccgcgcagcc ccgggtgacc ggcgtcgtcc tcttccggca gcttgcgccc    240
cgcgccaagc tcgacgcctt cttcgccctg gagggcttcc cgaccgagcc gaacagctcc    300
agccgcgcca tccacgtgca ccagttcggg gacctgagcc agggctgcga gtccaccggg    360
ccccactaca acccgctggc cgtgccgcac ccgcagcacc cgggcgactt cggcaacttc    420
gcggtccgcg acggcagcct ctggaggtac gcgccggcc tggccgcctc gctcgcgggc    480
ccgcactcca tcgtgggccg ggccgtggtc gtccacgctg gcgaggacga cctgggccgc    540
ggcggcaacc aggccagcgt ggagaacggg aacgcgggcc ggcggctggc ctgctgcgtg    600
gtgggcgtgt gcgggcccgg gctctgggag cgccaggcgc gggagcactc agagtga     657
```

<210> SEQ ID NO 18
<211> LENGTH: 696
<212> TYPE: DNA
<213> ORGANISM: Artificial Sequence
<220> FEATURE:
<223> OTHER INFORMATION: nucleotide sequence encoding R9-EC SOD fusion
    protein

<400> SEQUENCE: 18

```
cggcggcggc ggcggcggcg gcggcggtgg acgggcgagg actcggcgga gcccaactct     60
gactcggcgg agtggatccg agacatgtac gccaaggtca cggagatctg caggaggtc    120 atgcagcggc gggacgacga cggcacgctc cacgccgcct gccaggtgca gccgtcggcc    180
acgctggacg ccgcgcagcc ccgggtgacc ggcgtcgtcc tcttccggca gcttgcgccc    240
cgcgccaagc tcgacgcctt cttcgccctg gagggcttcc cgaccgagcc gaacagctcc    300
agccgcgcca tccacgtgca ccagttcggg gacctgagcc agggctgcga gtccaccggg    360
ccccactaca acccgctggc cgtgccgcac ccgcagcacc cgggcgactt cggcaacttc    420
```

```
gcggtccgcg acggcagcct ctggaggtac cgcgccggcc tggccgcctc gctcgcgggc    480
ccgcactcca tcgtgggccg ggccgtggtc gtccacgctg gcgaggacga cctgggccgc    540
ggcggcaacc aggccagcgt ggagaacggg aacgcgggcc ggcggctggc ctgctgcgtg    600
gtgggcgtgt gcgggcccgg gctctgggag cgccaggcgc gggagcactc agagcgcaag    660
aagcggcggc gcgagagcga gtgcaaggcc gcctga                              696

<210> SEQ ID NO 19
<211> LENGTH: 699
<212> TYPE: DNA
<213> ORGANISM: Artificial Sequence
<220> FEATURE:
<223> OTHER INFORMATION: nucleotide sequence encoding R9-EC SOD fusion
      protein

<400> SEQUENCE: 19
aagaagaaga agaagaagaa gaagaagaag tggacgggcg aggactcggc ggagcccaac     60
tctgactcgg cggagtggat ccgagacatg tacgccaagg tcacggagat ctggcaggag    120
gtcatgcagc ggcgggacga cgacggcacg ctccacgccg cctgccaggt gcagccgtcg    180
gccacgctgg acgccgcgca gccccgggtg accggcgtcg tcctcttccg gcagcttgcg    240
ccccgcgcca agctcgacgc cttcttcgcc ctggagggct tcccgaccga gccgaacagc    300
tccagccgcg ccatccacgt gcaccagttc ggggacctga ccagggctg cgagtccacc    360 gggcccact acaacccgct ggccgtgccg cacccgcagc accgggcga cttcggcaac    420 ttcgcggtcc gcgacggcag cctctggagg taccgcgccg gctggccgc ctcgctcgcg    480 ggcccgcact ccatcgtggg ccgggccgtg gtcgtccacg ctggcgagga cgacctgggc    540
cgcggcggca accaggccag cgtggagaac gggaacgcgg gccggcggct ggcctgctgc    600
gtggtgggcg tgtgcgggcc cgggctctgg gagcgccagg cgcgggagca ctcagagcgc    660
aagaagcggc ggcgcgagag cgagtgcaag gccgcctga                           699

<210> SEQ ID NO 20
<211> LENGTH: 68
<212> TYPE: DNA
<213> ORGANISM: Artificial Sequence
<220> FEATURE:
<223> OTHER INFORMATION: primer

<400> SEQUENCE: 20
tatgaaagaa acctggtggg aaacctggtg gaccgaatgg tctcagccga aaaaaaaacg     60
taaagtgc                                                             68

<210> SEQ ID NO 21
<211> LENGTH: 70
<212> TYPE: DNA
<213> ORGANISM: Artificial Sequence
<220> FEATURE:
<223> OTHER INFORMATION: primer

<400> SEQUENCE: 21
tcgabcactt tacgttttt tttcggctga gaccattcgg tccaccaggt ttcccaccag     60
gtttctttcc                                                           70

<210> SEQ ID NO 22
<211> LENGTH: 243
<212> TYPE: PRT
<213> ORGANISM: Artificial Sequence
<220> FEATURE:
```

<223> OTHER INFORMATION: Fusion protein having a protein transduction
domain PEP1 peptide fused to a human EC SOD (PEP1-EC SOD)

<400> SEQUENCE: 22

```
Lys Glu Thr Trp Trp Glu Thr Trp Trp Thr Glu Trp Ser Gln Pro Lys
1               5                   10                  15
Lys Lys Arg Lys Val Trp Thr Gly Glu Asp Ser Ala Glu Pro Asn Ser
            20                  25                  30
Asp Ser Ala Glu Trp Ile Arg Asp Met Tyr Ala Lys Val Thr Glu Ile
        35                  40                  45
Trp Gln Glu Val Met Gln Arg Arg Asp Asp Gly Thr Leu His Ala
    50                  55                  60
Ala Cys Gln Val Gln Pro Ser Ala Thr Leu Asp Ala Ala Gln Pro Arg
65                  70                  75                  80
Val Thr Gly Val Val Leu Phe Arg Gln Leu Ala Pro Arg Ala Lys Leu
                85                  90                  95
Asp Ala Phe Phe Ala Leu Glu Gly Phe Pro Thr Glu Pro Asn Ser Ser
            100                 105                 110
Ser Arg Ala Ile His Val His Gln Phe Gly Asp Leu Ser Gln Gly Cys
        115                 120                 125
Glu Ser Thr Gly Pro His Tyr Asn Pro Leu Ala Val Pro His Pro Gln
130                 135                 140
His Pro Gly Asp Phe Gly Asn Phe Ala Val Arg Asp Gly Ser Leu Trp
145                 150                 155                 160
Arg Tyr Arg Ala Gly Leu Ala Ala Ser Leu Ala Gly Pro His Ser Ile
                165                 170                 175
Val Gly Arg Ala Val Val Val His Ala Gly Glu Asp Asp Leu Gly Arg
            180                 185                 190
Gly Gly Asn Gln Ala Ser Val Glu Asn Gly Asn Ala Gly Arg Arg Leu
        195                 200                 205
Ala Cys Cys Val Val Gly Val Cys Gly Pro Gly Leu Trp Glu Arg Gln
    210                 215                 220
Ala Arg Glu His Ser Glu Arg Lys Lys Arg Arg Arg Glu Ser Glu Cys
225                 230                 235                 240
Lys Ala Ala
```

<210> SEQ ID NO 23
<211> LENGTH: 230
<212> TYPE: PRT
<213> ORGANISM: Artificial Sequence
<220> FEATURE:
<223> OTHER INFORMATION: Fusion protein having a protein transduction
domain PEP1 peptide fused to deltaHD/EC SOD deleted a heparin
domain from a human EC SOD (PEP1-deltaHD/EC SOD)

<400> SEQUENCE: 23

```
Lys Glu Thr Trp Trp Glu Thr Trp Trp Thr Glu Trp Ser Gln Pro Lys
1               5                   10                  15
Lys Lys Arg Lys Val Trp Thr Gly Glu Asp Ser Ala Glu Pro Asn Ser
            20                  25                  30
Asp Ser Ala Glu Trp Ile Arg Asp Met Tyr Ala Lys Val Thr Glu Ile
        35                  40                  45
Trp Gln Glu Val Met Gln Arg Arg Asp Asp Gly Thr Leu His Ala
    50                  55                  60
Ala Cys Gln Val Gln Pro Ser Ala Thr Leu Asp Ala Ala Gln Pro Arg
65                  70                  75                  80
```

Val Thr Gly Val Val Leu Phe Arg Gln Leu Ala Pro Arg Ala Lys Leu
                    85                  90                  95

Asp Ala Phe Phe Ala Leu Glu Gly Phe Pro Thr Glu Pro Asn Ser Ser
            100                 105                 110

Ser Arg Ala Ile His Val His Gln Phe Gly Asp Leu Ser Gln Gly Cys
        115                 120                 125

Glu Ser Thr Gly Pro His Tyr Asn Pro Leu Ala Val Pro His Pro Gln
    130                 135                 140

His Pro Gly Asp Phe Gly Asn Phe Ala Val Arg Asp Gly Ser Leu Trp
145                 150                 155                 160

Arg Tyr Arg Ala Gly Leu Ala Ala Ser Leu Ala Gly Pro His Ser Ile
                165                 170                 175

Val Gly Arg Ala Val Val His Ala Gly Glu Asp Asp Leu Gly Arg
            180                 185                 190

Gly Gly Asn Gln Ala Ser Val Glu Asn Gly Asn Ala Gly Arg Arg Leu
        195                 200                 205

Ala Cys Cys Val Val Gly Val Cys Gly Pro Gly Leu Trp Glu Arg Gln
210                 215                 220

Ala Arg Glu His Ser Glu
225                 230

<210> SEQ ID NO 24
<211> LENGTH: 737
<212> TYPE: DNA
<213> ORGANISM: Artificial Sequence
<220> FEATURE:
<223> OTHER INFORMATION: nucleotide sequence encoding PEP1-EC SOD fusion
      protein

<400> SEQUENCE: 24
tatgaaagaa acctggtggg aaacctggtg gaccgaatgg tctcagccga aaaaaaaacg      60
taaactgctg gacgggcgag gactcggcgg agcccaactc tgactcggcg gagtggatcc     120
gagacatgta cgccaaggtc acggagatct ggcaggaggt catgcagcgg cgggacgacg     180
acggcacgct ccacgccgcc tgccaggtgc agccgtcggc cacgctggac gccgcgcagc     240
cccgggtgac cggcgtcgtc ctcttccggc agcttgcgcc ccgcgccaag ctcgacgcct     300
tcttcgccct ggagggcttc ccgaccgagc cgaacagctc cagccgcgcc atccacgtgc     360
accagttcgg ggacctgagc cagggctgcg agtccaccgg gccccactac aacccgctgg     420
ccgtgccgca cccgcagcac ccgggcgact cggcaacttt cgcggtccgc gacggcagcc     480
tctggaggta ccgcgccggc ctggccgcct cgctcgcggg cccgcactcc atcgtgggcc     540
gggccgtggt cgtccacgct ggcgaggacg acctgggccg cggcggcaac caggccagcg     600
tggagaacgg gaacgcgggc cggcggctgg cctgctgcgt ggtgggcgtg tgcgggcccg     660
ggctctggga gcgccaggcg cgggagcact cagagcgcaa gaagcggcgg cgcgagagcg     720
agtgcaaggc cgcctga                                                   737

<210> SEQ ID NO 25
<211> LENGTH: 695
<212> TYPE: DNA
<213> ORGANISM: Artificial Sequence
<220> FEATURE:
<223> OTHER INFORMATION: nucleotide sequence encoding PEP1-deltaHD/EC
      SOD fusion protein

<400> SEQUENCE: 25
tatgaaagaa acctggtggg aaacctggtg gaccgaatgg tctcagccga aaaaaaaacg      60

-continued

```
taaactgctg gacgggcgag gactcggcgg agcccaactc tgactcggcg gagtggatcc    120
gagacatgta cgccaaggtc acggagatct ggcaggaggt catgcagcgg cgggacgacg    180
acggcacgct ccacgccgcc tgccaggtgc agccgtcggc cacgctggac gccgcgcagc    240
cccgggtgac cggcgtcgtc ctcttccggc agcttgcgcc ccgcgccaag ctcgacgcct    300
tcttcgccct ggagggcttc ccgaccgagc cgaacagctc cagccgcgcc atccacgtgc    360
accagttcgg ggacctgagc cagggctgcg agtccaccgg gccccactac aacccgctgg    420
ccgtgccgca cccgcagcac ccgggcgact cggcaacttc gcggtccgc gacggcagcc     480 tctggaggta ccgcgccggc ctggccgcct cgctcgcggg cccgcactcc atcgtgggcc    540
gggccgtggt cgtccacgct ggcgaggacg acctgggccg cggcggcaac caggccagcg    600
tggagaacgg gaacgcgggc cggcggctgg cctgctgcgt ggtgggcgtg tgcgggcccg    660
ggctctggga gcgccaggcg cgggagcact cagag                                695
```

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
ttgtctctaa tagagggtc    19

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
tcaagcctgt ctatcttct    19

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
atctacagct cctttggtct t    21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atctacagct cctttggctt    20

<210> SEQ ID NO 30
<211> LENGTH: 20
<212> TYPE: DNA
<213> ORGANISM: Artificial Sequence
<220> FEATURE:
<223> OTHER INFORMATION: primer

```
-continued

<400> SEQUENCE: 30
aaccctcaga gccacccta                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gtgcatacaa agcaaactgc                                             20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
catcttccag gagcgagacc                                             20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
tccaccaccc tgttgctgta                                             20
```

EC SOD AND CELL TRANSDUCING EC SOD AND USE THEREOF

This application is a national stage application, filed under 35 U.S.C. §371, of PCT/KR2004/002757, filed on Oct. 29, 2004, which claims priority to Korean Patent Application No. KR 10-2003-0076629, filed Oct. 31, 2003.

TECHNICAL FIELD

The present invention relates to an extracellular superoxide dismutase (EC SOD), a cell-transducing EC SOD, and the use thereof. More particularly, the present invention relates to an EC SOD, a cell-transducing EC SOD with enhanced cell-transduction ability, and the use thereof for preventing or treating skin diseases.

BACKGROUND ART

Superoxide dismutase (SOD) is one family of antioxidant enzyme that functions to remove damaging reactive oxygen species from cellular environment and to protect cells. SOD functions to dismutation of two superoxide radical to hydrogen peroxide and oxygen. SOD is classified into Cu/Zn SOD containing copper and zinc atoms, Mn SOD containing manganese atom, and extracellular superoxide dismutase (EC SOD) located in the cell surface or the extracellular fluid. Of them, EC SOD contains copper and zinc atoms as in Cu/Zn SOD, but is characterized in that a heparin-binding domain is present in the C-terminal end. Since EC SOD has the heparin-binding domain, it is assumed that EC SOD will finction to protect cell membranes by binding to the cell membranes. According to literatures, it was known that EC SOD plays a role in the body's defense mechanism in serums and extracellular matrices (Marklund et al, _Biochem. J._ 266, 213-219, 1990; Su et al., _Am J Respir Cell Mol Biol._, February 16(2), 162-70, 1997; Luoma et al., _Thromb. Vasc. Bio._ 18, 157-167, 1998). Other literatures reported that gene therapy with EC SOD improves aorta restenosis in rabbits and alleviates collagen-induced arthritis in mice (Laukkanen M O et al., _Circulation,_ 106, 1999-2003, 2002; Iyama S et al., _Arthritis & Rheumatism,_ 44, 9, 2160-2167, 2001). Recently, it was reported that EC SOD could inhibit telomere shortening, a cell aging phenomenon in human fibroblasts and extends the replicative life span of human fibroblast (Serra V et al., _J. Biol. Chem.,_ 278, 9, 6824-6830, 2003). In addition, it was reported that the heparin-binding domain of EC SOD acts as a nuclear localization signal so that it is located within the nuclei of thymuses and testis cells so as to protect genomic DNA from oxidative stress and to regulate the DNA transcription sensitive to oxidation-reduction reaction (Ookawara T et al., _BBRC,_ 296, 54-61, 2002). However, neither the distribution pattern of EC SOD in the skin nor the effect of EC SOD on skin diseases is yet known.

Meanwhile, as the fact that certain proteins can effectively enter cells through cellular membranes is found, studies to use such proteins as transport means to transduce useful substances into cells are now actively performed. Typical examples of such proteins include HIV Tat protein, ANTP, VP22 protein, PEP-1 peptide, and the like (Lindgren et al., _TIPS_ 21:99, 2001; Green et al., _Cell,_ 55, 1179-1188, 1988)). It is known that the cell-transduction ability of such proteins is caused by the properties of a protein transduction domain (PTD) with the activity capable of crossing a cell membrane phospholipid bilayer (Fankel A. D. et al., _Cell,_ 55, 1189-1193, 1988; Green M. et al., _Cell,_ 55, 1179-1188, 1988).

Accordingly, since drugs or proteins which are used as therapeutic agents cannot spontaneously cross the cell membrane in most cases, studies to use the above-described protein transduction domain to introduce useful proteins into cells are now performed.

DISCLOSURE OF THE INVENTION

Therefore, during studies on the activity of EC SOD, the present inventors have discovered new facts that EC SOD is more present in the dermal layer of the body skin than in the epidermal layer while it removes reactive oxygen species in skin cells and inhibits the overgrowth of epidermal cells, the expression of matrix metalloproteinase (MMP) and the degranulation of mast cells. Thus, the present inventors have found that EC SOD can be used for preventing and treating skin diseases, and also, the present inventors prepared an EC SOD fusion protein with cell-transduction ability by fusing a protein transduction domain to EC SOD. On the basis of this discovery and preparation, the present invention has been perfected.

Accordingly, an object of the present invention is to provide a pharmaceutical composition for preventing or treating skin disease, which comprises as an active ingredient an isolated EC SOD protein or an expression vector comprising a polynucleotide encoding the protein.

Another object of the present invention is to provide a cosmetic composition for preventing or improving of skin diseases, which comprises an isolated EC SOD protein.

Still another object of the present invention is to provide a method for preventing or treating skin diseases, which comprises administering to a subject in need thereof an effective amount of an isolated EC SOD protein or an expression vector comprising a polynucleotide encoding the protein.

Still another object of the present invention is to provide the use of an isolated EC SOD protein or an expression vector comprising a polynucleotide encoding the protein, for the preparation of a pharmaceutical composition for preventing or treating skin diseases.

Still another object of the present invention is to provide a pharmaceutical composition for preventing or treating skin diseases, which comprises either a cell-transducing EC SOD fusion protein in which a protein transduction domain is fused to an EC SOD protein or a polynucleotide encoding the protein.

Still another object of the present invention is to provide a cosmetic composition for preventing or improving skin diseases, which comprises an isolated cell-transducing EC SOD fusion protein in which a protein transduction domain is fused to an EC SOD protein.

Still another object of the present invention is to provide a method for preventing or treating skin diseases, which comprises administering to a subject in need thereof an effective amount of either an isolated cell-transducing EC SOD fusion protein in which a protein transduction domain is fused to an EC SOD protein or an expression vector comprising a polynucleotide encoding the fusion protein.

Still another object of the present invention is to provide the use of either an isolated cell-transducing EC SOD fusion protein in which a protein transduction domain is fused to an EC SOD protein or an expression vector comprising a polynucleotide encoding the fission protein, for the preparation of a pharmaceutical composition for preventing or treating skin diseases.

Yet another object of the present invention is to provide a cell-transducing EC SOD fusion protein in which a protein transduction domain fused to the amino terminal end of EC SOD.

Another further object of the present invention is to provide a polynucleotide encoding the fusion protein.

To achieve the above objects, the present invention provides a pharmaceutical composition for preventing or treating skin diseases, which comprises as an active ingredient an isolated EC SOD protein or an expression vector comprising a polynucleotide encoding the protein.

Also, the present invention provides a cosmetic composition for preventing or improving skin diseases, which comprises an isolated EC SOD protein.

Also, the present invention provides a method for preventing or treating skin diseases, which comprises administering to a subject in need thereof an effective amount of an isolated EC SOD protein or an expression vector comprising a polynucleotide encoding the protein.

Also, the present invention provides the use of an isolated EC SOD protein or an expression vector comprising a polynucleotide encoding the protein, for the preparation of a pharmaceutical composition for preventing or treating skin diseases.

Also, the present invention provides a pharmaceutical composition for preventing or treating skin diseases, which comprises either a cell-transducing EC SOD fusion protein in which a protein transduction domain is fused to an EC SOD protein or an expression vector comprising a polynucleotide encoding the protein.

Also, the present invention provides a cosmetic composition for preventing or improving skin diseases, which comprises an isolated cell-transducing EC SOD fusion protein in which a protein transduction domain is fused to an EC SOD protein.

Also, the present invention provides a method for preventing or treating skin diseases, which comprises administering to a subject in need thereof an effective amount of either an isolated cell-transducing EC SOD fusion protein in which a protein transduction domain is fused to an EC SOD protein or an expression vector comprising a polynucleotide encoding the fusion protein.

Also, the present invention provides the use of either an isolated cell-transducing EC SOD fusion protein in which a protein transduction domain is fused to an EC SOD protein or an expression vector comprising a polynucleotide encoding the fusion protein, for the preparation of a pharmaceutical composition for preventing or treating skin diseases.

Also, the present invention provides a cell-transducing EC SOD fusion protein in which a protein transduction domain is fused to the amino terminal end of EC SOD.

Also, the present invention provides a polynucleotide encoding the fusion protein.

Hereinafter, the present invention will be described in detail.

In one example of the present invention, the distribution pattern of EC SOD in the mouse skin was examined by immunohistochemical staining (see Example 1-1). The examination results could suggest that EC SOD is distributed throughout the mouse skin, and particularly, more present in the connective tissue of the dermal layer than in the epidermal layer (see FIG. 1). Also, in another example of the present invention, the expression pattern of EC SOD mRNA in the dermal and epidermal layers of the skin was examined (see Example 1-2), and as a result, a new fact that EC SOD is expressed at a much higher level in the dermal layer than in the epidermal layer could be found (see FIG. 2). From the above experimental results, it was inferred that EC SOD would perform the action of protecting the skin while it would be present in the skin tissue, particularly the dermal layer.

Accordingly, in order to directly examine the role of EC SOD in the skin, in one example of the present invention, the mouse skin was irradiated with various UV lights (UVA, UVB and PUVA), and the expression patterns of EC SOD were analyzed at varying time points after the UV irradiation (see Examples 1-3 to Examples 1-5). The results could indicate that the expression of EC SOD in the skin varies depending on the presence or absence of UV irradiation (see FIGS. 3 to 5).

From the above experimental results, the present inventors have found a new fact that EC SOD is distributed throughout the skin tissue, particularly the dermal layer, while its expression varies with UV irradiation intensity and the passage of time.

Also, the present inventors examined the effect of overexpression of EC SOD on the amount of UV-induced intracellular reactive oxygen by preparing a mouse EC SOD-overexpressed cell line, irradiating the cell with UV and then measuring the amount of reactive oxygen in the cell (see Example 2). The results could suggest that the overexpression of mouse EC SOD effectively reduces intracellular reactive oxygen (see FIGS. 6 and 7).

Moreover, the present inventors examined the effect of overexpression of human EC SOD on UV-induced cell death by preparing a human EC SOD-overexpressed cell line, irradiating the cell with UV and then measuring cell death (see Example 3). The results could indicate that the overexpression of human EC SOD effectively reduces cell death induced by UV (see FIG. 9).

On this, in order to facilitate the protecting action of EC SOD on the skin tissue, the present inventors imparted cell-transduction ability to EC SOD by preparing a EC SOD fusion protein where a protein transduction domain is, selected from an HIV-1 Tat transduction domain (amino acid residues 49-57), an oligopeptide consisting of 5-12 arginine residues, an oligopeptide consisting of 5-12 lysine residues, and a PEP-1 peptide had been bound to EC SOD (see Example 4).

Furthermore, the present inventors more concretely examined the therapeutic effects of EC SOD and cell-transducing EC SOD in skin disease models with TPA (12-O-tetradecanoylphorbol-13-acetate).

The TPA induces inflammations with the dermal infiltration of lymphocyte and neutrophils, and interfollicular epidermal hyperplasia in mouse skin cells, so as to cause skin diseases such as dermatitis and psoriasis (Segal et al., *Cancer Res*, 35:2154-2159, 1975; Sawa et al., *J Med Chem*, 45:930-936, 2002). Furthermore, TPA treatment can promote aging process by activating a MMP (matrix metalloproteinase) enzyme which decomposes connective tissues released from keratinocytes. Thus, the present inventors examined the expression pattern of EC SOD in the TPA-treated skin tissue of mice where EC SOD has been overexpressed in the skin, as well as a change in the thickness of the skin tissue. Also, the expression of MMP was examined in EC SOD-overexpressed keratinocyte cells and human fibroblasts which treated either an EC SOD protein or a cell-transducing EC SOD fusion protein (see Example 5). The results could suggest that the EC SOD and the cell-transducing EC SOD fusion protein inhibit the overgrowth of epidermal cells (see FIGS. 20 and 21) and the activity of an MMP (matrix metalloproteinase) enzyme (see FIGS. 22 and 23). Thus, it could be found that these proteins have the effect of preventing or inhibiting the development of skin diseases, such as dermatitis, psoriasis-like epidermal hyperplasia, and aging.

Furthermore, the present inventors examined whether the EC SOD protein inhibits the degranulation of the mast cells with the inventive EC SOD protein (see Example 6). It is known that if the mast cells are degranulated, chemical substances will be released from the mast cells so as to cause allergic skin diseases, such as atopy, contact allergy and urticaria. The test results showed that the inventive EC SOD protein could inhibit the degranulation of mast cells so as to effectively prevent and treat the above-described allergic skin diseases (see Table 3).

From the test results as described above, the present inventors could found a new fact that the EC SOD and the cell-transducing EC SOD have the activity capable of effectively preventing or treating skin diseases by removing intracellular reactive oxygen species, inhibiting the overgrowth of epidermal cells, the expression of MMP (matrix metalloproteinase) and the degranulation of mast cells.

Thus, the present invention provides a pharmaceutical composition for preventing or treating skin diseases, which comprises as an active ingredient the EC SOD protein or the cell-transducing EC SOD fusion protein.

The EC SOD proteins which can be used in the present invention include a natural or recombinant EC SOD protein or a protein with the substantially equivalent physiological activity to the EC SOD protein. The protein with the substantially equivalent physiological activity includes functional equivalents and derivatives of the natural/recombinant EC SOD protein. The EC SOD protein can be prepared using known nucleic acid sequences by genetic engineering methods, and an illustration of a method for the preparation of this protein is described in an example of the present invention.

As used herein, the term "functional equivalents" refers to proteins which exhibit substantially equivalent physiological activity to the natural EC SOD protein and have at least 60%, preferably at least 70%, and more preferably at least 90% sequence homology, to the amino acid sequence of natural EC SOD protein. The functional equivalents include, for example, amino acid sequence variants having a substitution of some amino acids or all amino acids of the natural protein or a deletion or addition of some amino acids of the natural protein. The substitution of amino acids is preferably a conservative substitution. Examples of a conservative substitution of naturally occurring amino acids include: aliphatic amino acids (Gly, Ala, Pro), hydrophobic amino acids (Ile, Leu, Val), aromatic amino acid (Phe, Tyr, Trp), acidic amino acids (Asp, Glu), basic amino acids (His, Lys, Arg, Gln, Asn), and sulfur-containing amino acids (Cys, Met). The deletion of amino acids is located at a portion which is not involved directly in the physiological activity of the EC SOD protein.

As used herein, the term "functional derivatives" refers to proteins with physical and chemical modifications for increasing or reducing the physical and chemical properties of the EC SOD protein. Derivatives with modifications for changing the temperature stability, storage stability, solubility and pH stability of the EC SOD protein are within the scope of the present invention. The functional derivatives of the EC SOD protein are made by any method known in the art.

The amino acid sequence of the inventive EC SOD protein is known in the art and derived from mammals. Preferably, the mammals include human beings. Most preferably, the inventive EC SOD protein is defined as a protein consisting of an amino acid sequence of SEQ ID NO: 11. Furthermore, the EC SOD protein may be a protein in which the heparin transduction domain (amino acid residues 210-222) is deleted.

The cell-transducing EC SOD fusion protein according to the present invention is characterized in that the protein transduction domain is fused to the amino terminal end of an isolated EC SOD protein or a protein exhibiting substantially equivalent physiological activity to the EC SOD protein and having at least 60% sequence homology of the amino acid sequence of the EC SOD protein. The protein transduction domain refers to an oligopeptide consisting of several amino acid residues, which is able to introduce not only itself but also polymeric organic compounds, such as other kinds of oligonucleotides, peptides, proteins and oligosaccharides, without requiring separate receptors or energy into the cell. Examples of the protein transduction domain which can be used in the present invention include, but are not specifically limited to, an HIV-1 Tat transduction domain, an oligopeptide consisting of 5-12 arginine residues, an oligopeptide consisting of 5-12 lysine residues, a PEP-1 peptide, an ANTP protein, a VP22 protein, and the like (Morris et al., *Nat Biotechnol*, 19:1173-1175, 2001; Schwarze et al., *Trends Cell Biol*, 10:290-295, 2000; Vives et al., *J Biol Chem* 272:16010-16017, 1997). Preferably, one selected from the group consisting of a transduction domain of 9 amino acid residues (RKKRRQRRR) corresponding to amino acids 49-57 of HIV-1 Tat, an oligopeptide of 9 arginine residues, an oligopeptide of 10 lysine residues, and a PEP-1 peptide (KETWWETWWTEWSQPKKKRKV), may be used as the protein transduction domain.

The HIV-1 Tat transduction domain is characterized by having a signal to open the lipid barrier of cells to be transduced by EC SOD. The hydrophobic domain of the PEP-1 peptide binds to the hydrophobic portion of a protein to be transduced and then plays a role of increasing the efficiency of targeting the protein to the cell membrane, and the hydrophilic domain plays a role of facilitating the movement of the protein into the cytoplasm.

Meanwhile, definitions of abbreviations used in the present invention are as follows: R (alanine); Q (glutamine); E (glutamic acid); K (lysine); P (proline); S (serine); T (threonine); W (tryptophan); V (valine).

Most preferably, the cell-transducing EC SOD fusion protein according to the present invention may be selected from a TAT-EC SOD fusion protein, a TAT-ΔHD/EC SOD fusion protein, a K10-EC SOD fusion protein, an R9-EC SOD fusion protein, a PEP1-EC SOD fusion protein, and a PEP1-ΔHD/EC SOD fusion protein, which have amino acid sequences of SEQ ID NO: 12, SEQ ID NO: 13, SEQ ID NO: 14, SEQ ID NO: 15, SEQ ID NO: 22 and SEQ ID NO: 23, respectively.

Skin diseases against which the inventive EC SOD proteins can be applied include all those caused by reactive oxygen species, the overgrowth of epidermal cells, the expression of MMP (matrix metalloproteinase), or degranulation of mast cells. Examples of the skin diseases may include, but are not limited to, skin cancer, pigmentation disease, photoaging, chronoaging, dermatitis, atopy, contact allergy, epidermal hyperplasia, and urticaria.

The inventive pharmaceutical composition may comprise a pharmaceutically acceptable carrier together with the EC SOD protein or the cell-transducing EC SOD fusion protein. As used herein, the term "pharmaceutically acceptable carrier" refers to a substance that is physiologically acceptable and does not generally cause allergic reactions, such as gastrointestinal disorder and dizziness etc. or reactions similar thereto when administered into humans.

The pharmaceutically acceptable carriers may include, for example, carriers for oral administration or for parenteral administration. The carriers for oral administration may include lactose, starch, cellulose derivatives, magnesium stearate, stearic acid and so on. Also, the carriers for parenteral administration may include water, suitable oils, saline solution, aqueous glucose and glycol etc. and the inventive composition may further comprise stabilizers and conservatives. Suitable stabilizers include antioxidants, such as sodium bisulfite, sodium sulfite or ascorbic acid. Suitable preservatives include benzalkonium chloride, methyl- or propyl-paraben, and chlorobutanol. For other pharmaceutically acceptable carriers, reference may be made to the following literature: Remington's Pharmaceutical Sciences, 19th ed., Mack Publishing Company, Easton, Pa., 1995.

The EC SOD protein or the cell-transducing EC SOD fusion protein, which is contained in the inventive composition, may be formulated into various parenteral or oral dosage forms, together with the pharmaceutically acceptable carrier as described above. The formulations for parenteral administration preferably include injection formulations, such as isotonic aqueous solution or suspension formulations, and ointment formulations. The injection formulations may be prepared using suitable dispersing or wetting agents, and suspending agents, according to the known methods in the art. For example, each ingredient is dissolved in saline or buffer and then can be prepared into a dosage form for injection. Examples of the formulations for oral administration include, but are not limited to, powders, granules, tablets, pills and capsules, and these formulations may comprise, in addition to the active ingredient, diluents (e.g., lactose, dextrose, sucrose, mannitol, sorbitol, cellulose, and/or glycin) and lubricants (e.g., silica, talc, stearic acid, and magnesium or calcium salts thereof, and/or polyethylene glycol). The tablets may comprise binders, such as magnesium aluminum silicate, starch paste, gelatin, tragacanth, methyl cellulose, sodium carboxymethylcellulose and/or polyvinylpyrrolidone, and if necessary, it may further comprise disintegrants, such as starch, agar-agar, alginate or a sodium salt thereof, or azeotropic mixtures and/or absorbing agents, coloring agents, flavoring agents and sweetening agents. These formulations may be prepared by a conventional mixing, granulation or coating method.

Routes for the administration of the inventive pharmaceutical composition include, but are not limited to, oral, intravenous, intramuscular, intraarterial, intramarrow, intrathecal, intracardiac, transdermal, epicutaneous, subcutaneous, intraperitoneal, intranasal, intestinal tract, local, sublingual and rectal routes.

Preferably, the pharmaceutical composition according to the present invention can be administered parenterally by a subcutaneous, intravenous, intramuscular, intraarticular, intrabursal, intrasternal, intrathecal, intralesional or intracranial injection or infusion technique. For example, the inventive pharmaceutical composition formulated for injection may be administered by messotherapy which is the method of injection into the skin at a given amount by a fine needle of 4-6 mm or lightly pricking the skin with a 30-gage injection needle. Also, for application to the skin, the inventive pharmaceutical composition may be formulated into, for example, ointment preparations, in the transdermal or epicutaneous administration. As used herein, the term "transdermal or epicutaneous administration" means that the pharmaceutical composition is locally administered into the skin such that an effective amount of an active ingredient contained in the pharmaceutical composition is transferred. Particularly, a pharmaceutical composition containing the inventive cell-transducing EC SOD fusion protein as an active ingredient is preferably administered by the transdermal or epicutaneous administration technique for direct application to the skin.

Furthermore, the inventive pharmaceutical composition may be administered by a bioengineering technique associated with a protein transduction method.

The EC SOD protein or cell-transducing EC SOD fusion protein contained in the pharmaceutical composition according to the present invention may be administered to a patient at an amount showing a preventive or therapeutic effect. Generally, this EC SOD protein may be administered at a daily dose ranging from about 0.0001 to 100 mg/kg, and preferably about 0.01 to 1 mg/kg. The inventive pharmaceutical compositions may be administered at an amount within the preferred daily dose range one time or several times each day. However, the dose of the inventive pharmaceutical composition may be suitably selected according to an administration route, a subject to be administered, and the age, sex, body weight, characteristic and disease condition of the subject.

In another aspect, the present invention provides a pharmaceutical composition for preventing or treating skin diseases, which comprises as an active ingredient an expression vector comprising either a polynucleotide encoding the EC SOD protein or a polynucleotide encoding the cell-transducing EC SOD fusion protein.

The polynucleotide encoding the EC SOD protein may preferably be one encoding an amino acid sequence of SEQ ID NO: 11.

The polynucleotide encoding the cell-transducing EC SOD fusion protein is characterized in that a DNA sequence encoding a protein transduction domain is bound to the 5'-terminal end of EC SOD cDNA. The DNA sequence encoding the protein transduction domain may be a DNA sequence encoding one selected from an HIV-1 Tat transduction domain, an oligopeptide consisting of 5-12 arginine residues, an oligopeptide consisting of 5-12 lysine residues, a PEP-1 peptide, an ANTP protein, and a VP22 protein, but is not limited thereto. Also, the inventive polynucleotide may be one in which the 5' terminal end of protein transduction domain fused EC SOD protein is bounded to a DNA sequence encoding six histidine residue. Preferably, the polynucleotide sequence encoding the inventive fusion protein may be one of SEQ ID NO: 16, SEQ ID NO: 17, SEQ ID NO: 18, SEQ ID NO: 19, SEQ ID NO: 24 or SEQ ID NO: 25.

The expression vector comprising the polynucleotide sequence may contain an expression control sequence together with the polynucleotide encoding the EC SOD protein or the polynucleotide encoding the cell-transducing EC SOD fusion protein. As used herein, the term "expression control sequence" refers to DNA sequences necessary for the expression of operably linked coding sequences in a certain host cell. The expression control sequences include promoters for performing transcription, optional operator sequences for controlling the transcription, sequences encoding suitable mRNA ribosome-binding sites, and transcriptional and translational termination regulatory sequences. For example, control sequences suitable for prokaryotic organisms include promoters, operator sequences, and sequences encoding ribosome-bind sites. Eukaryotic cells are known to utilize promoters, polyadenylation signals, and enhancers.

The expression vector contained in the inventive pharmaceutical composition may be a plasmid or virus vector, and refers to a vector which can be introduced into a target cell in an expressed state by any method known in the art, such as infection or transduction.

A plasmid expression vector is a means for transferring plasmid DNA directly to human cells by a gene transfer method approved by FDA for use in human beings (Nabel E G, et al., *Science*, 249:1285-1288, 1990). Plasmid expression vectors which can be used in the present invention include mammalian expression plasmids known in the art. Typical examples include, but are not limited to, pRK5 (European Patent No. 307,247), pSV16B (PCT publication No. 91/08291) (PharMingen) and pVL1392 (PharMingen).

The plasmid expression vector may be introduced into a target cell by any method known in the art, such as transient transfection, microinjection, transduction, cell fusion, calcium phosphate precipitation, liposome-mediated transfection, DEAE dextran-mediated transfection, polybrene-mediated transfection, electroporation, gene gun or other methods for introducing DNA into cells (Wu et al., *J Biol Chem*, 267:963-967, 1992; Wu and Wu, *J Biol Chem*, 263:14621-14624, 1988).

Moreover, the virus expression vectors according to the present invention include, but are not limited to, retrovirus, adenovirus, herpes virus and avipox virus.

The virus vector may be administered by any method known in the art. For example, it may be administered by a local, parenteral, oral, intranasal, intravenous, intramuscular or subcutaneous route or any other suitable route. Particularly, the vector may be injected directly into a target cell in an effective amount.

In still another aspect, the present invention provides a method for preventing or treating skin diseases, which comprises administering to a subject in need thereof an effective amount of the EC SOD protein, the cell-transducing EC SOD fusion protein, or a polynucleotide encoding each of the proteins.

As used herein, the term "effective amount" refers to an amount showing the effect of preventing or treating skin diseases.

As used herein, the term "subject" means animals including mammals, particularly human beings. The subject may be a patient requiring treatment.

In yet another aspect, the present invention provides the use of the EC SOD protein, the cell-transducing EC SOD fusion protein, or a polynucleotide encoding each of the proteins, for the preparation for a pharmaceutical composition for preventing or treating skin diseases.

In another further aspect, the present invention provides a cosmetic composition comprising the isolated EC SOD protein or isolated cell-transducing EC SOD fusion protein of the present invention. The inventive cosmetic composition may be very effectively used against aging or pigmentation diseases, such as, discoloration or melasma, dermatitis, psoriasis, atopy, urticaria and allergy. The aging diseases include all natural aging and photoaging. The natural aging refers to aging that naturally occurs with advancing years, and the photoaging refers to aging that occurs by artificial or natural exposure to UV, etc. In addition, the inventive cosmetic composition is effective in the prevention and improvement of wrinkles caused by aging.

The functional cosmetic composition according to the present invention may be prepared by a conventional method. The inventive EC SOD protein may be contained in an amount of 0.001-50% by weight, and preferably 0.1-20% by weight, based on the dry weight of the cosmetic composition.

Along with dermatologically acceptable carriers, the inventive cosmetic composition may be applied in foundation cosmetic compositions (e.g., toilet water, cream, essence, cleansing foam, cleansing water, pack, and body oil), color cosmetic compositions (e.g., foundation, lipstick, mascara, and make-up base), and the like. Such carriers may include skin softener, skin penetration enhancers, coloring agents, aromatics, emulsifiers, thickeners, and solvents.

In still another aspect, the present invention provides a cell-transducing EC SOD fusion protein in which a protein transduction domain is fused to the EC SOD protein. The cell-transducing EC SOD fusion protein can transducer into skin cells, thus increasing the therapeutic effect of the EC SOD protein against skin diseases.

In yet another aspect, the present invention provides a polynucleotide sequence encoding the EC SOD fusion protein.

The cell-transducing EC SOD fusion protein may be prepared by the steps of: (a) transforming a host microorganisms with a recombinant expression vector comprising a polynucleotide sequence encoding the cell-transducing EC SOD fusion protein; (b) culturing the transformed microorganisms prepared in the step (a) in a suitable medium and condition for the expression of the polynucleotide sequence; and (c) collecting a substantially pure fusion protein encoded by the polynucleotide sequence from the culture solution of the step (b).

As the host microorganisms, any microorganisms can be used without special limitations if they can express the cell-transducing EC SOD fusion protein of the present invention. Examples of such host microorganism include bacteria, such as *E. coli, bacillus, Pseudomonas* and *Streptomyces*, eukaryotic and prokaryotic host cells, such as fungi and yeasts, insect cells, such as *Spodoptera frugiperida* (SF9), animal cells, such as CHO and mouse cells, and tissue-cultured human and plant cells. Preferred microorganisms include bacteria such as *E. coli* and *bacillus subtilis*. Depending on applications, microorganisms for food proved to be safe in the human body, such as lactic acid bacteria, may be used.

Left: a photograph showing the result of immunostaining with a rabbit anti-mouse EC SOD antibody.

Right: a photograph showing the result of immunostaining with preimmune rabbit serum as a negative control group.

Figure 2:
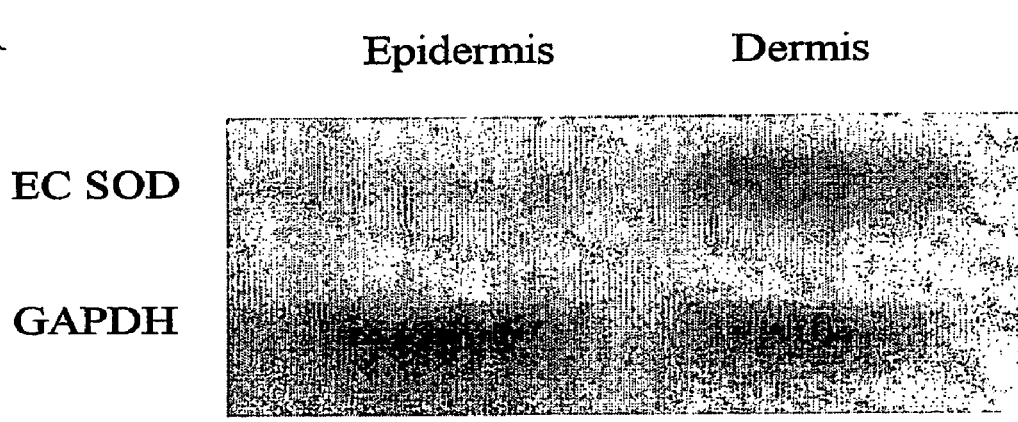
Figure 2:
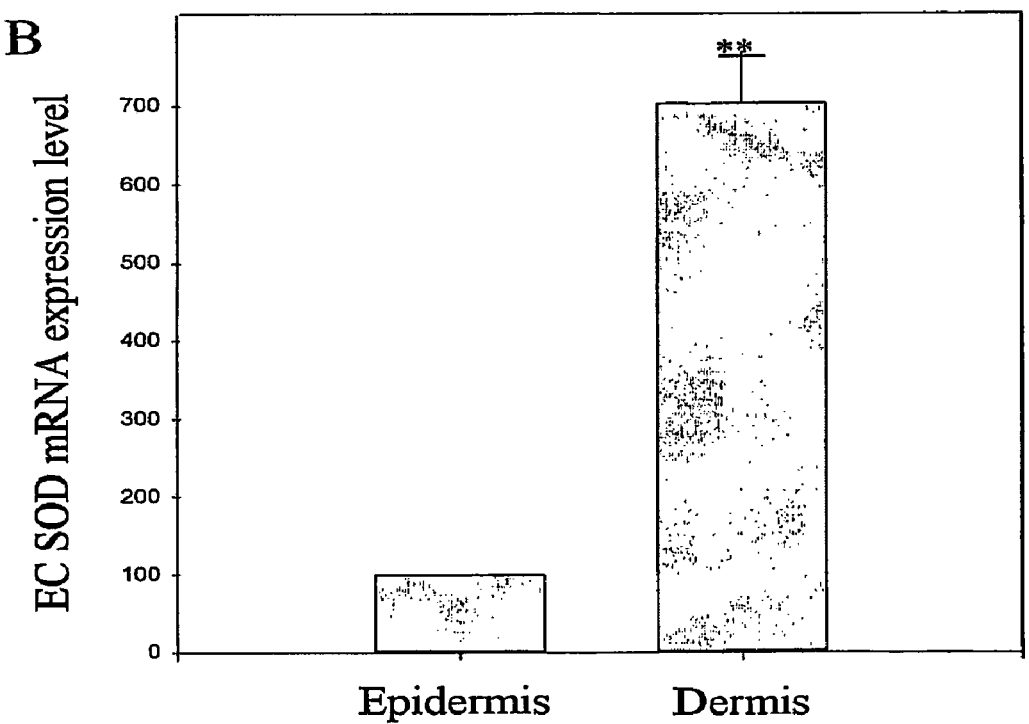

FIG. 2 shows the results of Northern blot analysis for the expression pattern of EC SOD in the epidermal and dermal layers of the mouse skin. GAPDH was used as a loading control.

**: significant difference at $p<0.05$.

Figure 3:
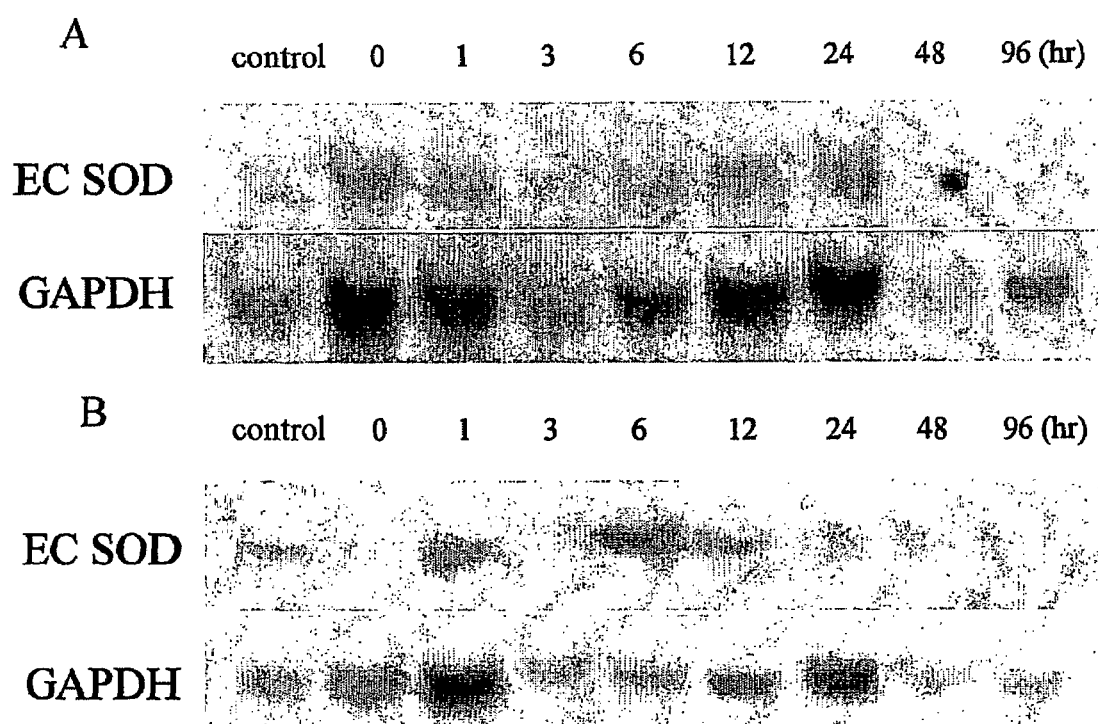

FIG. 3 shows the results of Northern blot analysis for the expression pattern of EC SOD in mice at different time points after UVA irradiation. GAPDH was used a loading control.

A: 5 $kJ/m^2$ of irradiation
B: 25 $kJ/m^2$ of irradiation

Figure 4:
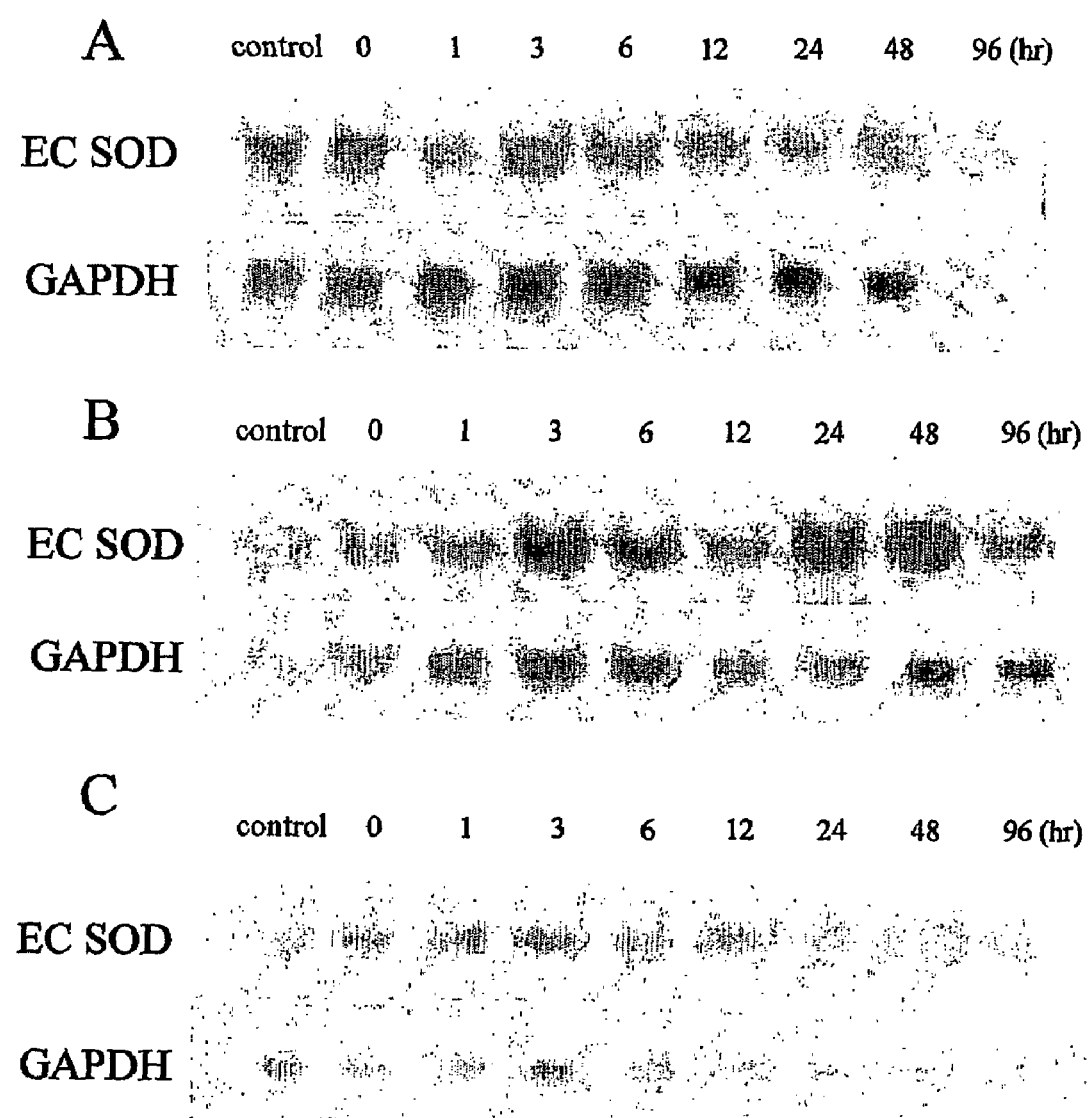

FIG. 4 shows the results of Northern blot analysis for the expression of EC SOD in mice at different time points after UVB irradiation. GAPDH was used as a loading control.

Figure 5:
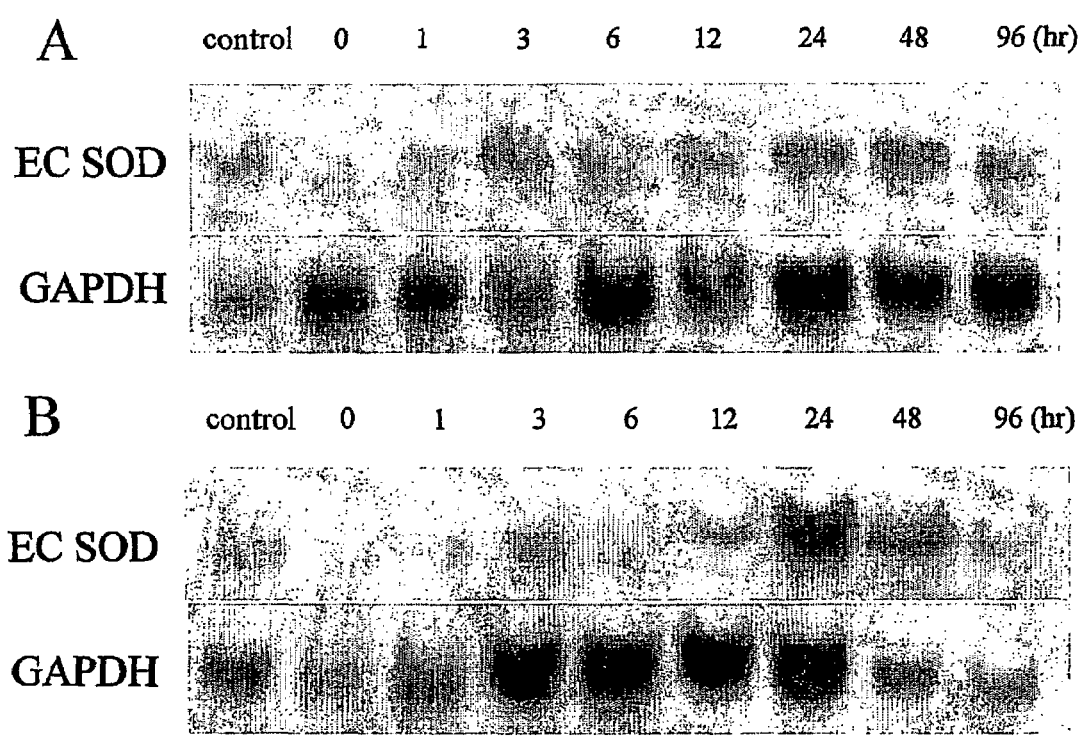

A: 2 $kJ/m^2$ of irradiation
B: 8 $kJ/m^2$ of irradiation
C: 15 $kJ/m^2$ of irradiation FIG. 5 shows the results of Northern blot analysis for the expression of EC SOD in mice at different time points after the mice are treated with 8-MOP and, after one hour, irradiated with UVA.

A: 5 $kJ/m^2$ of irradiation
B: 25 $kJ/m^2$ of irradiation

Figure 6:
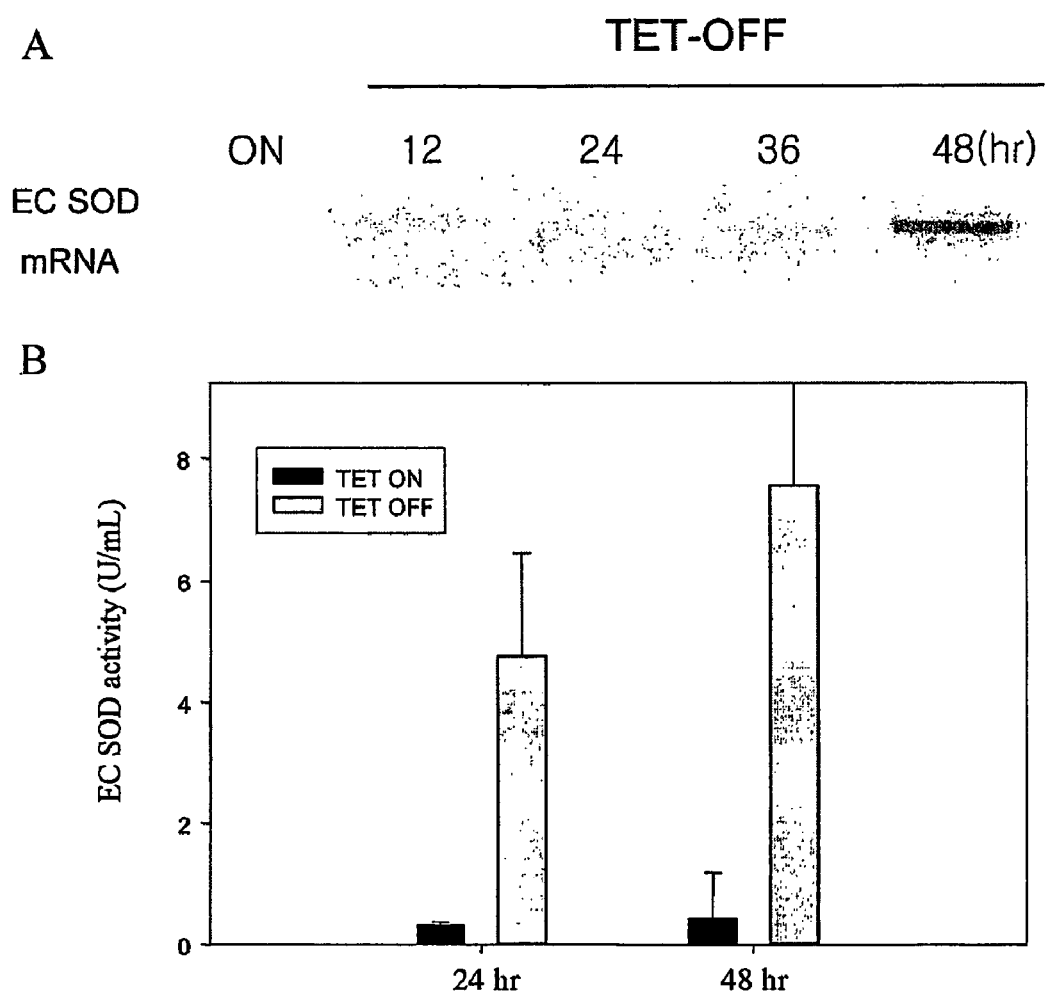

FIG. 6 shows the results of Northern blot analysis for the expression pattern of EC SOD (A) at different time points after removing tetracycline from a Tet off-MEF/3T3 inducible gene expression system (TET OFF) to induce the overexpression of EC SOD, as well as the activity of EC SOD (B).

Figure 7A:
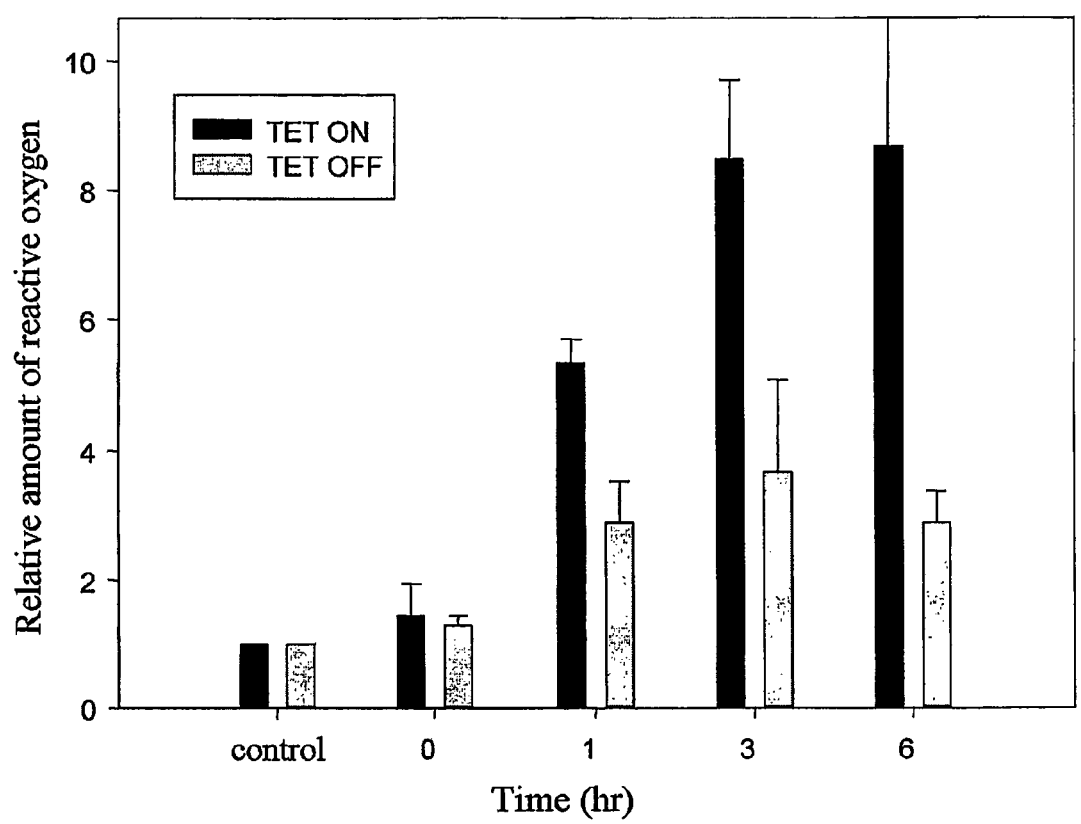

TET ON: the case of presence of tetracycline
TET OFF: the case of removal of tetracycline FIG. 7A is a graph showing, as a value relative to that of a control group, the amount of intracellular reactive oxygen species in a mouse EC SOD-overexpressed cell line at different time points after irradiation with 10 J/cm$^2$ of UVA.

Figure 7B:
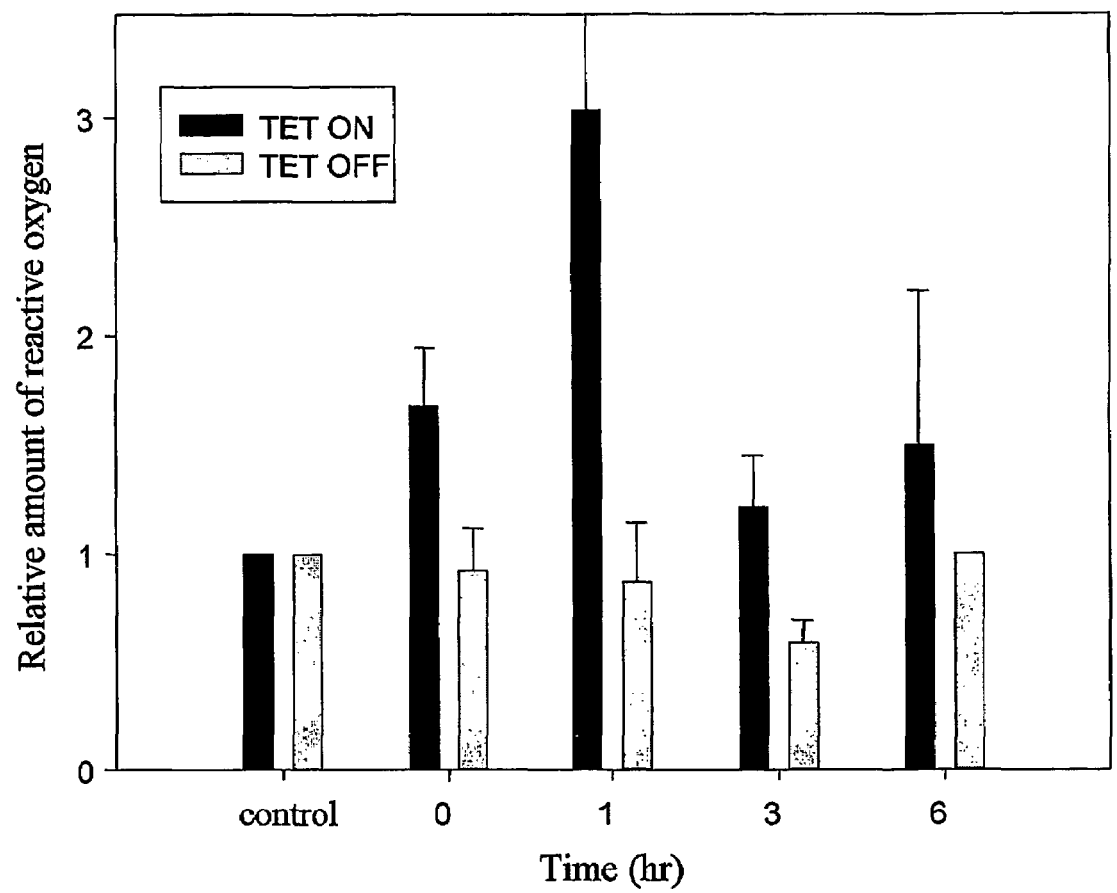

TET ON: the case of presence of tetracycline
TET OFF: the case of removal of tetracycline FIG. 7B is a graph showing, as a value relative to that of a control group, the amount of intracellular reactive oxygen species in a mouse EC SOD-overexpressed cell line at different time points after irradiation with 20 mJ/cm$^2$ of UVB.

Figure 7C:
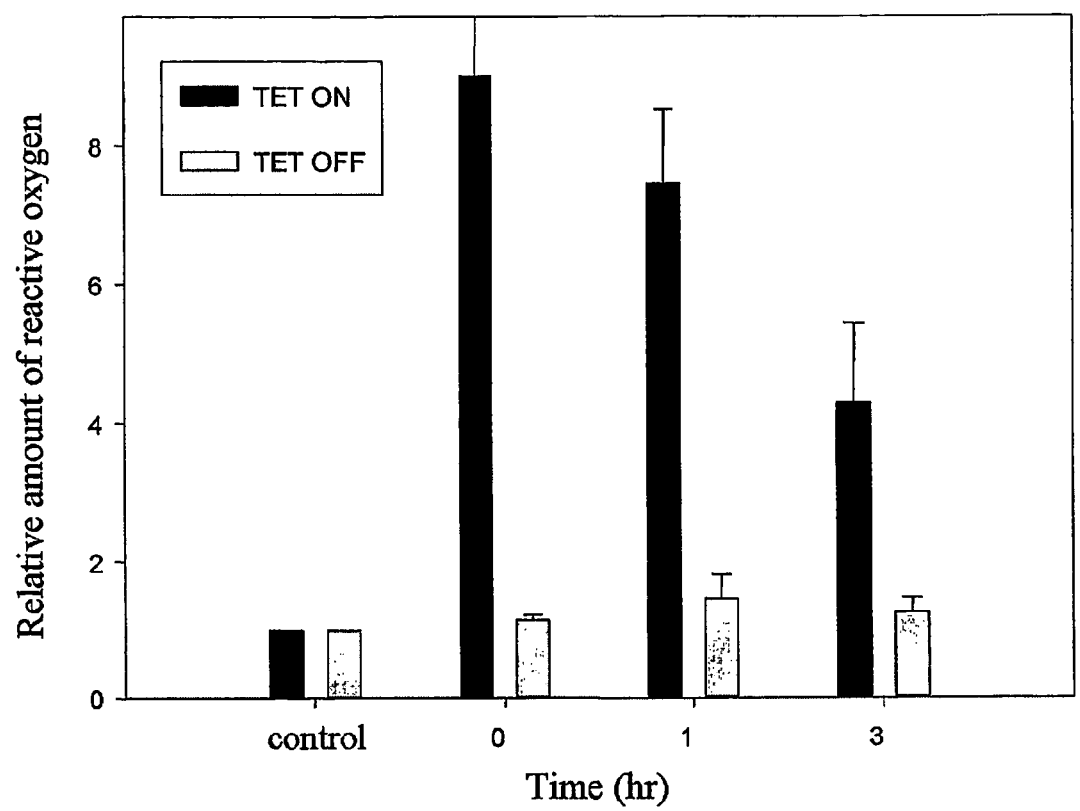

TET ON: the case of presence of tetracycline
TET OFF: the case of removal of tetracycline FIG. 7C is a graph showing, as a value relative to that of a control group, the amount of intracellular active oxygen in a mouse EC SOD-overexpressed cell line at different time points after the cell line is treated with 0.1% 8-MOP and, after 30 minutes, irradiated with 2 J/cm$^2$ of UVA.

Figure 8:
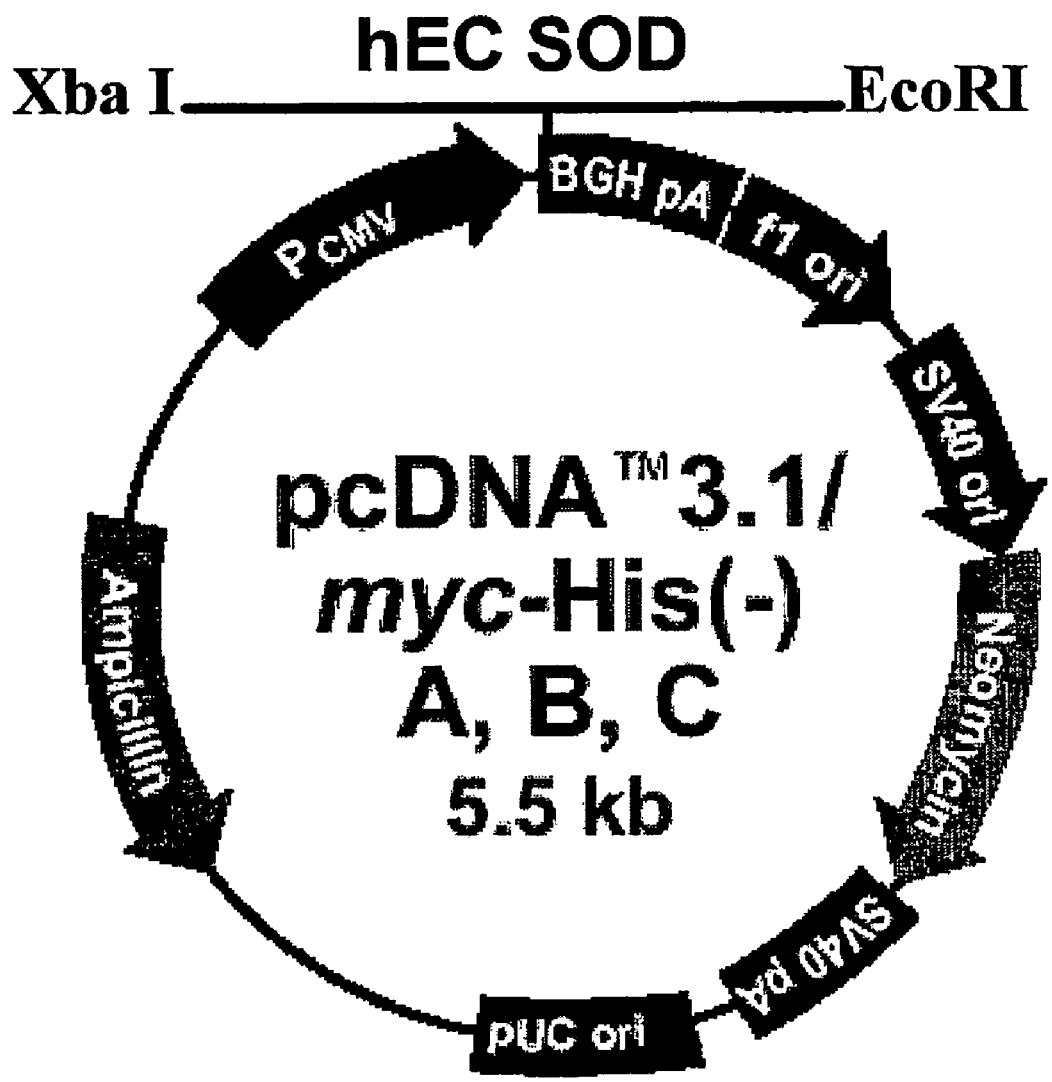

TET ON: the case of presence of tetracycline
TET OFF: the case of removal of tetracycline FIG. 8 shows a restriction map of a human EC SOD overexpression vector according to the present invention.

Figure 9:
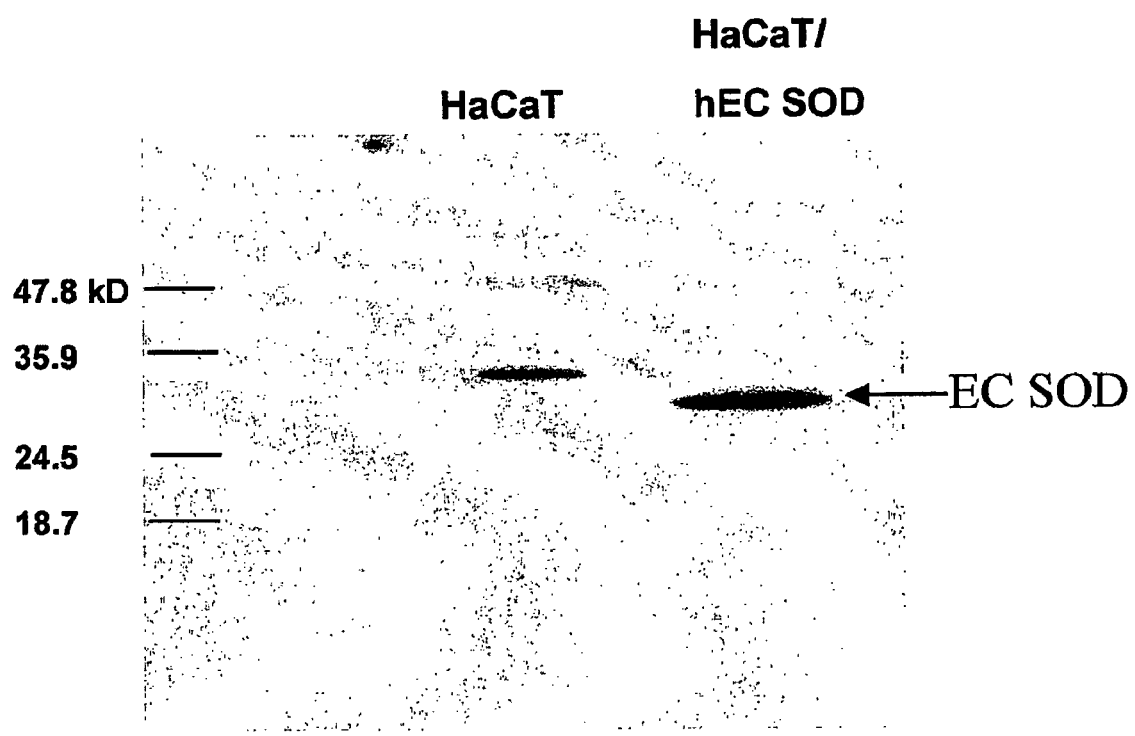

FIG. 9 shows the result of Western blot analysis for EC SOD expressed in EC SOD-overexpressed HaCaT cells.

Figure 10:
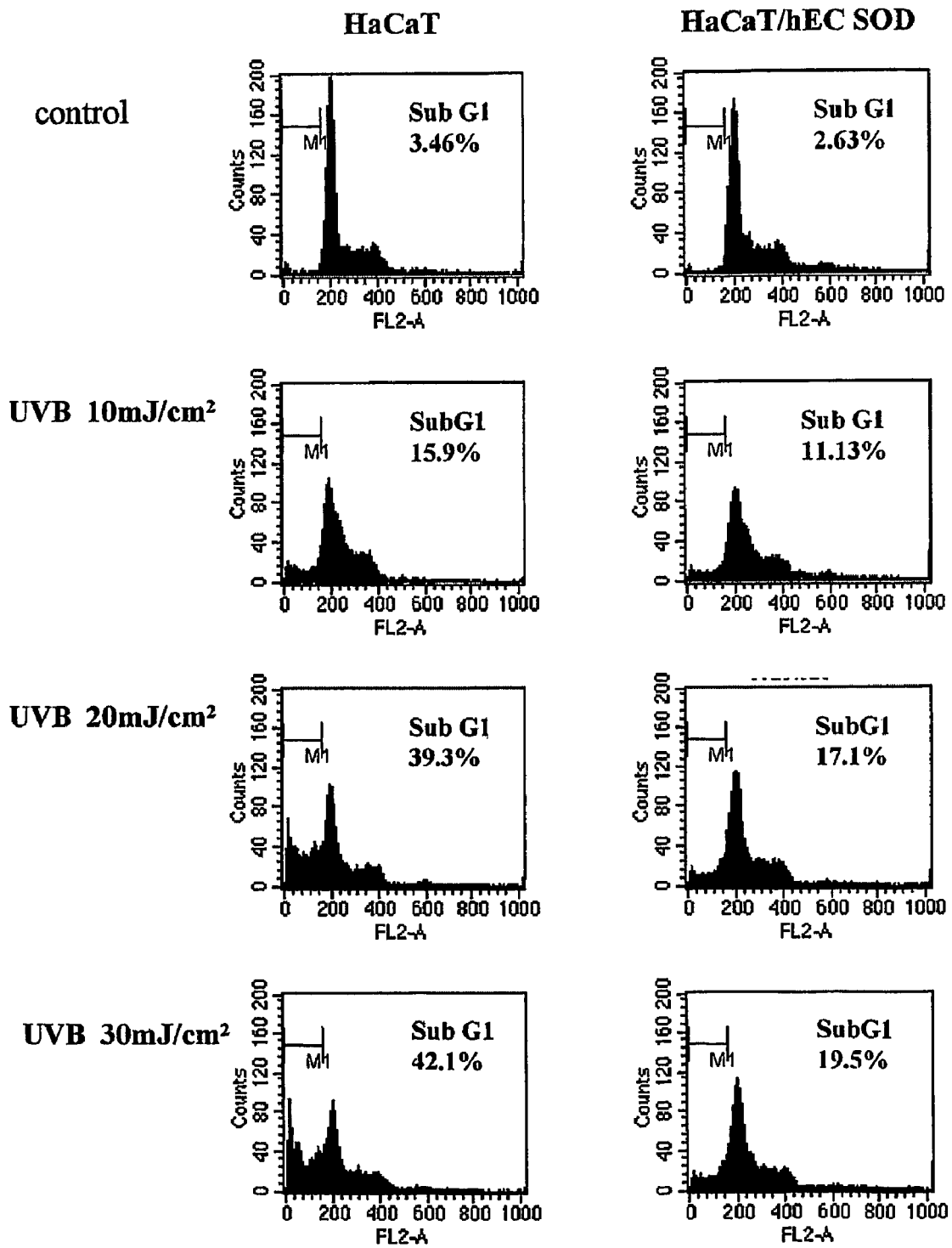

FIG. 10 shows the results of flow cytometric analysis for the ratio of cell death resulted from UV irradiation on EC SOD-overexpressed HaCaT cells.

Figure 11:
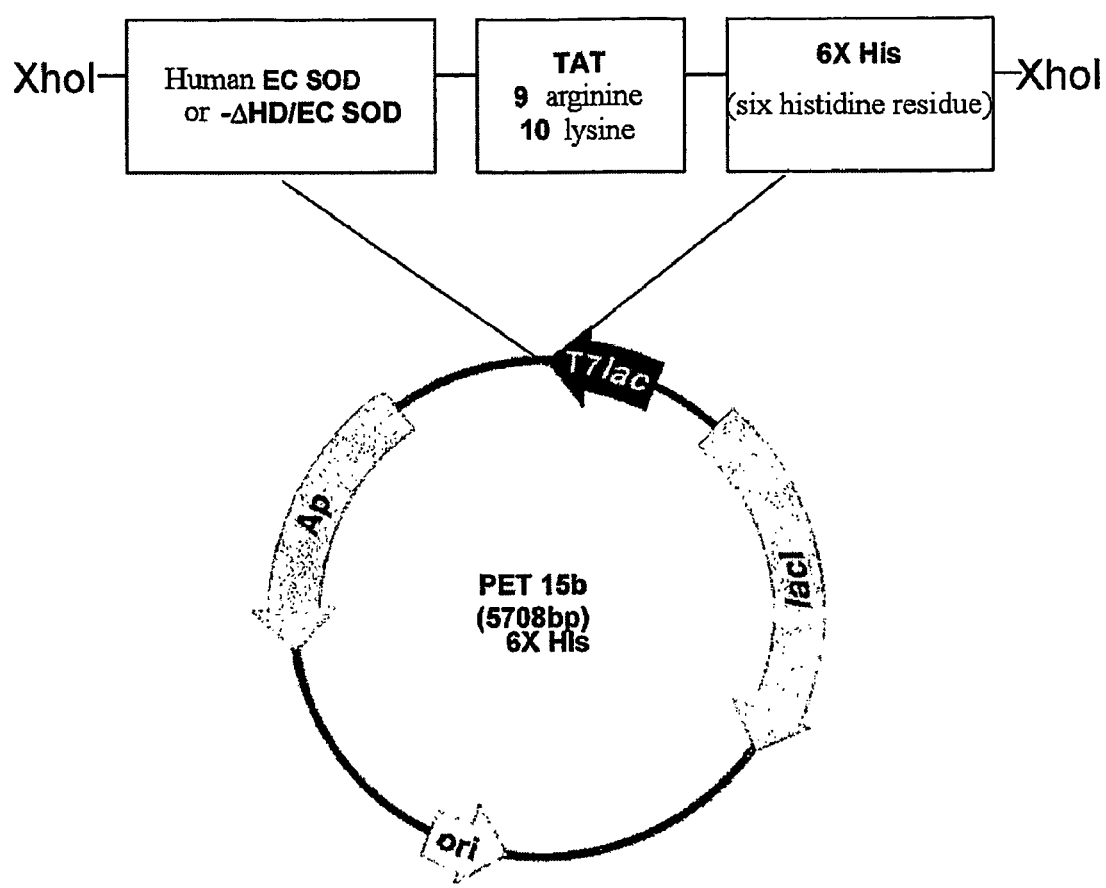

FIG. 11 shows a restriction map of a TAT-EC SOD fusion protein or TAT-ΔHD/EC SOD fusion protein expression vector according to the present invention.

Figure 12:
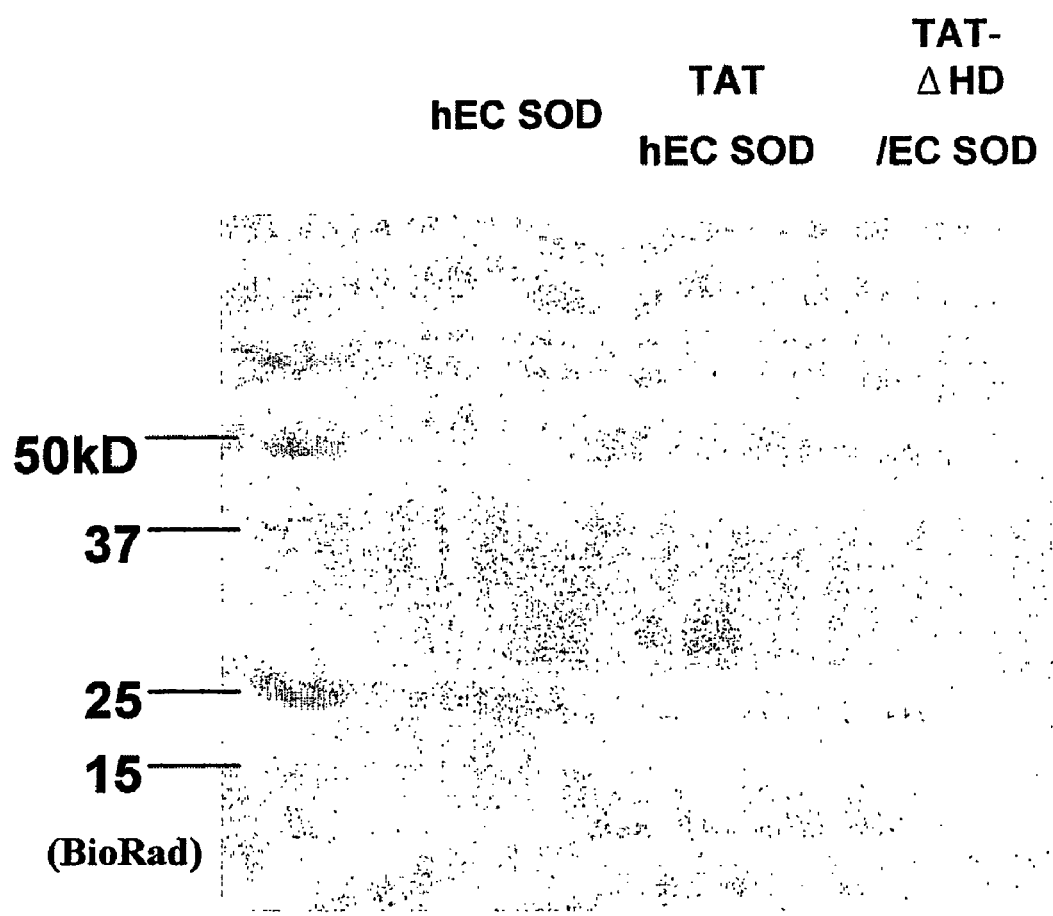

FIG. 12 is a photograph showing the results of electrophoresis analysis for a purified TAT-EC SOD fusion protein and TAT-ΔHD/EC SOD fusion protein.

Figure 13:
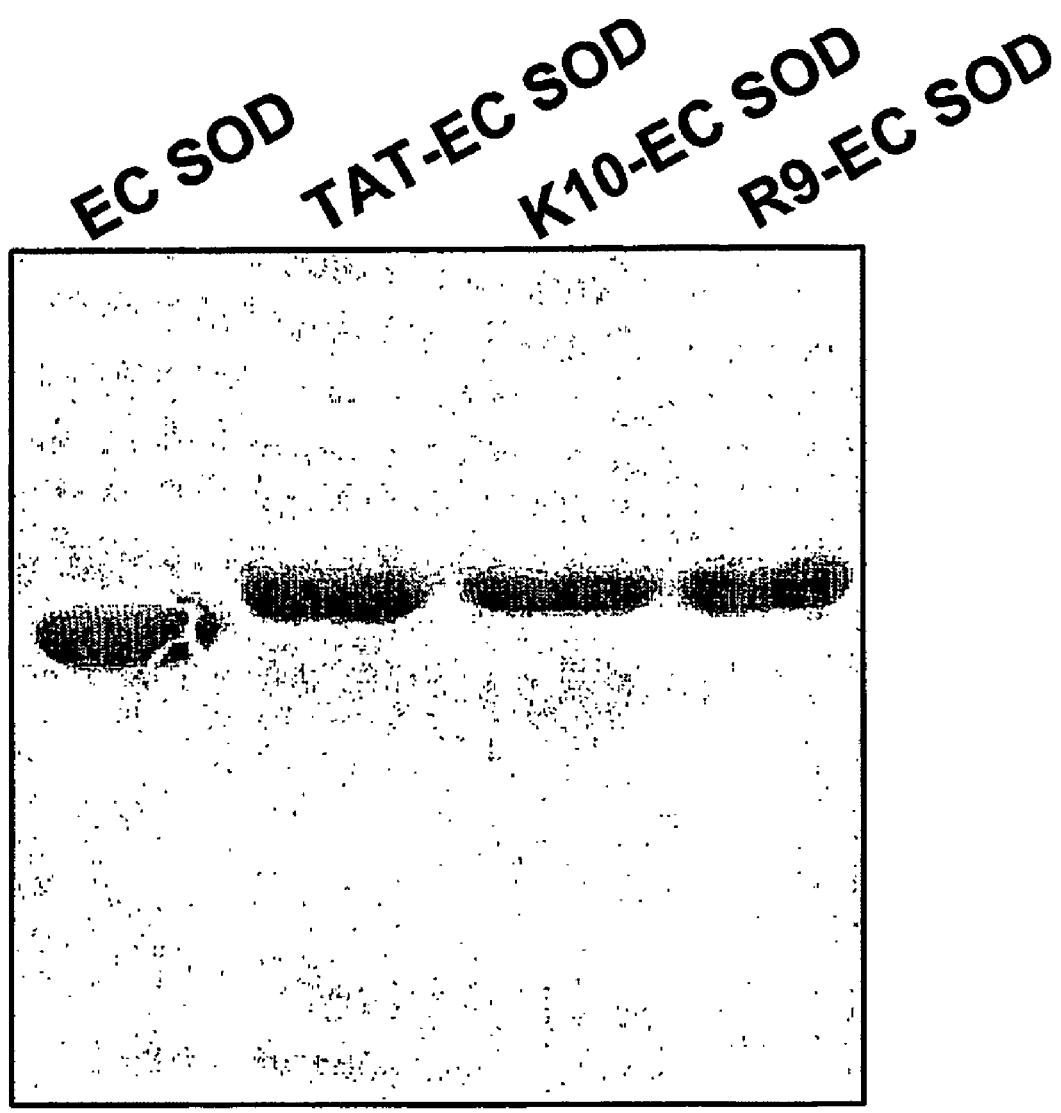

FIG. 13 is a photograph showing the results of electrophoresis for a purified TAT-EC SOD fusion protein, K10-EC SOD fusion protein and R9-EC SOD fusion protein.

Figure 14:
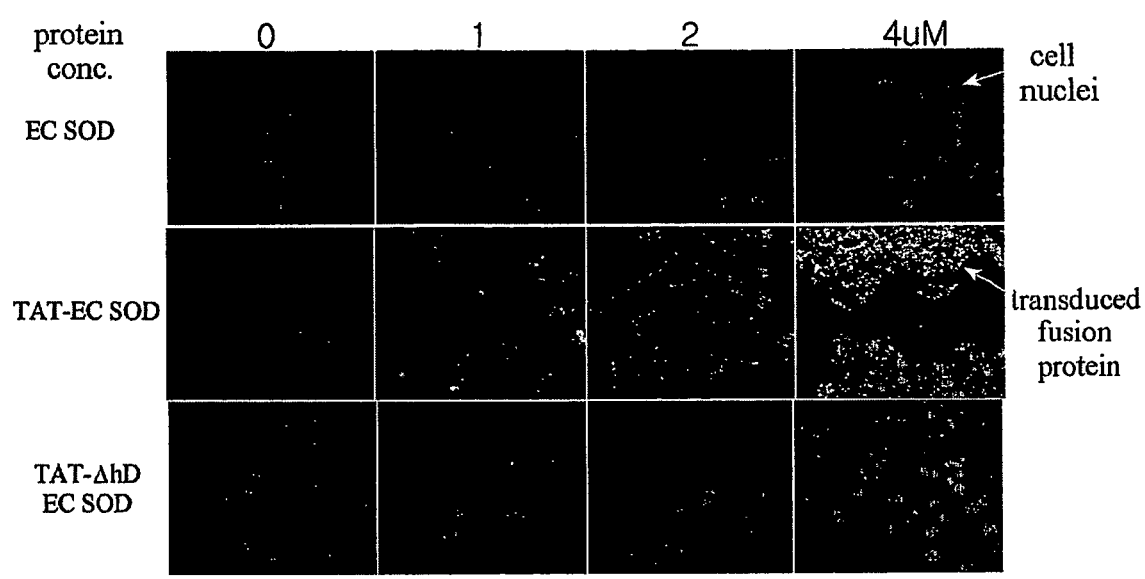

FIG. 14 is a photograph showing the results of immunocytochemical observation indicating that a TAT-EC SOD fusion protein and TAT-ΔHD/EC SOD fusion protein of the present invention transduce into human HaCaT cells so that they are located within the cell nuclei.

Figure 15:
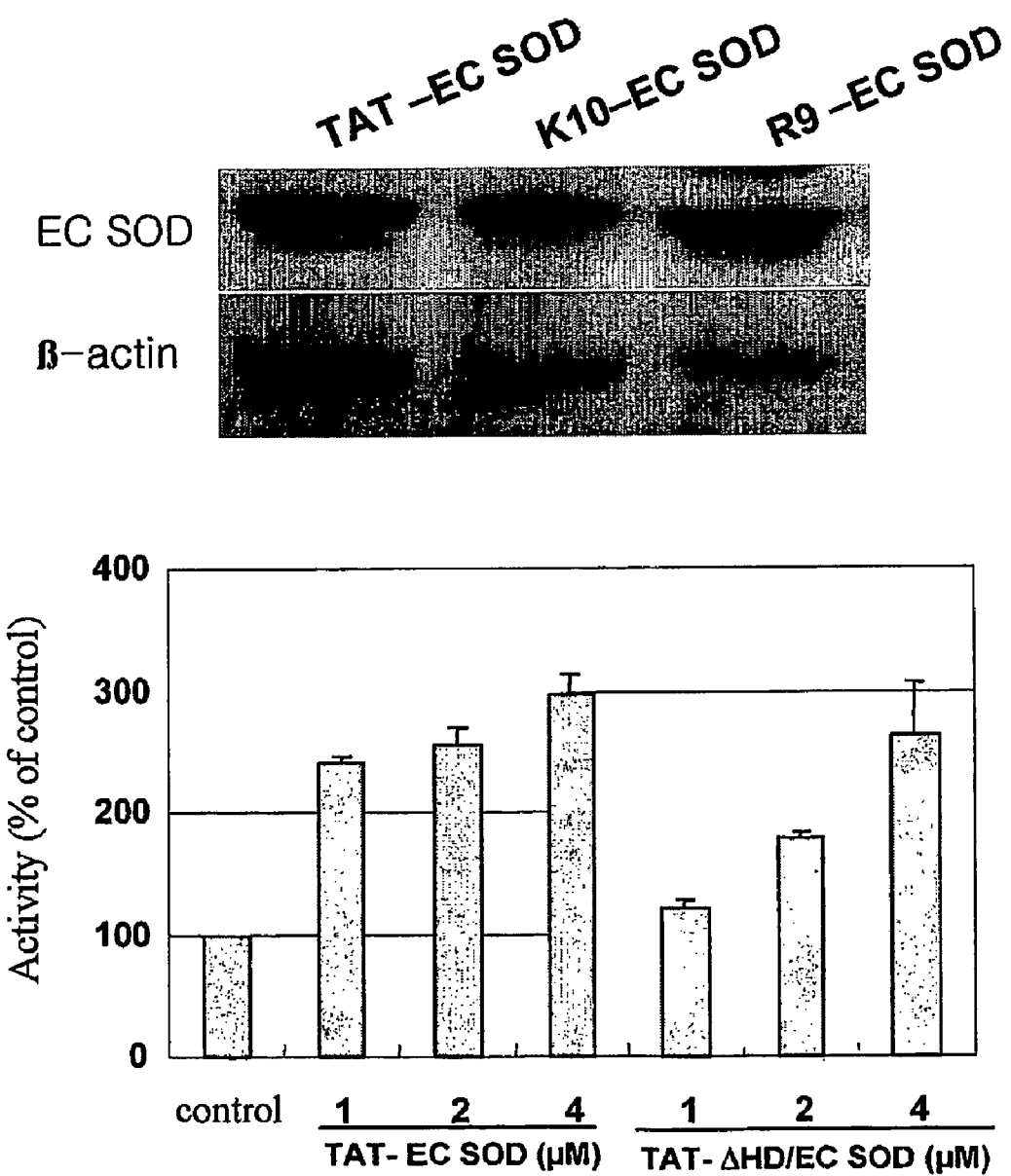

FIG. 15 shows the results of Western blot analysis for the cell transduction efficiencies of a TAT-EC SOD fusion protein and TAT-ΔHD/EC SOD fusion protein of the present invention.

Figure 16:
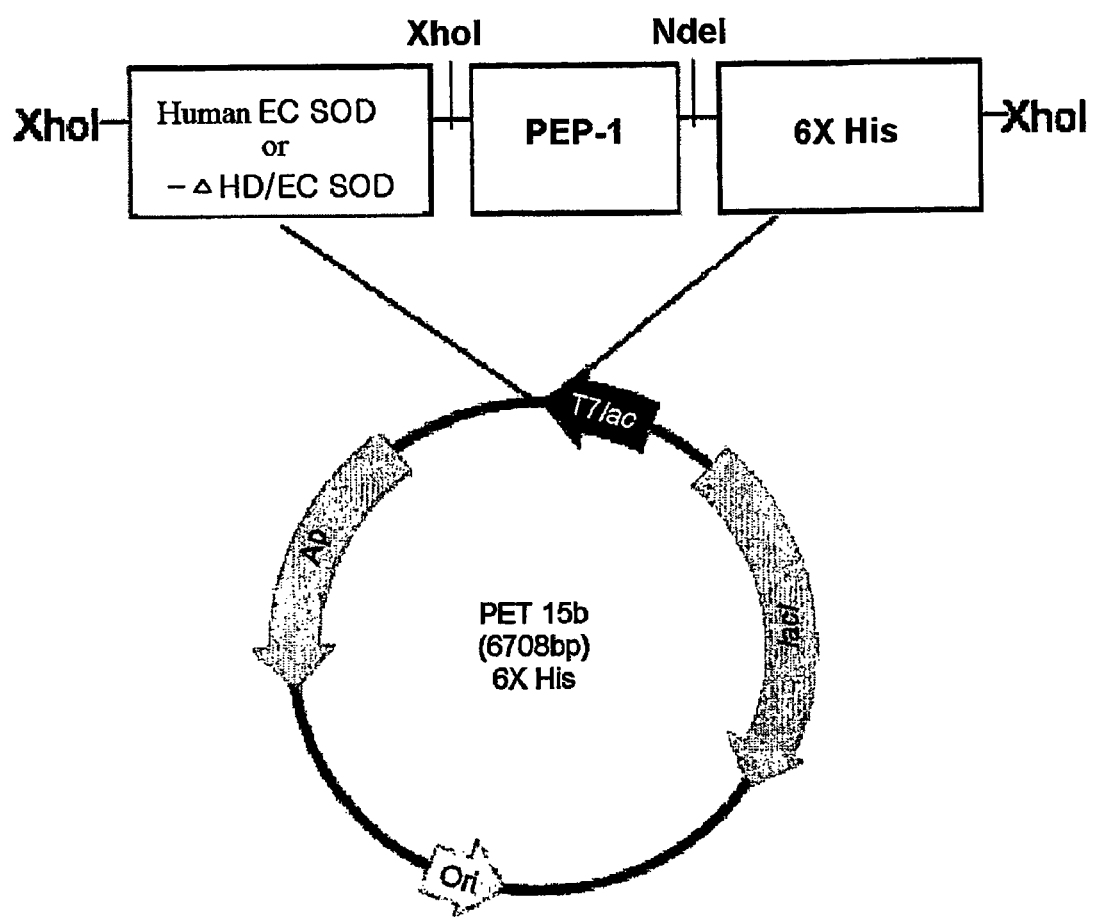

FIG. 16 shows a restriction map of a PEP1-EC SOD fusion protein or PEP1-ΔHD/EC SOD fusion protein expression vector of the present invention.

Figure 17:
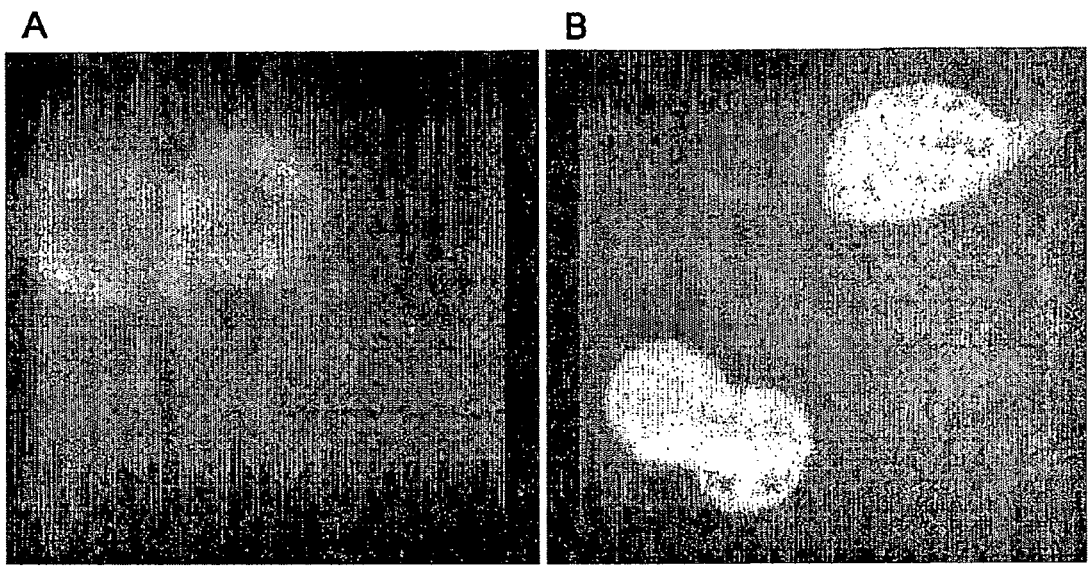

FIG. 17 is a photograph showing the results of immunocytochemical observation indicating that a PEP1-EC SOD fusion protein of the present invention transduces into HeLa cells so that it is located within the cell nuclei.

A: an EC SOD protein-treated group (negative control group); and
B: a PEP-1-EC SOD fusion protein-treated group (test group).

Figure 18:
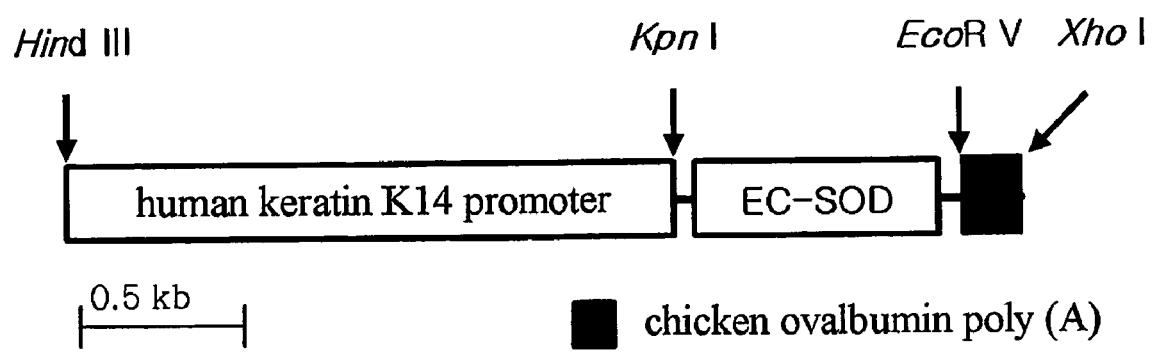

FIG. 18 is a schematic diagram of a mouse EC SOD overexpression vector used for the preparation of EC SOD-overexpressed mice.

Figure 19:

FIG. 19 shows the results of immunohistochemical analysis for the expression pattern of EC SOD in the skin tissue of TPA-treated wild-type mice and EC SOD-overexpressed mice.

A: the skin tissue of wild-type mice;
B: the skin tissue of EC SOD-overexpressed mice;
e: epidermal layer; d: dermal layer; arrow: follicular cell;
size bar: 100 μm; and magnification: 100×

Figure 20:
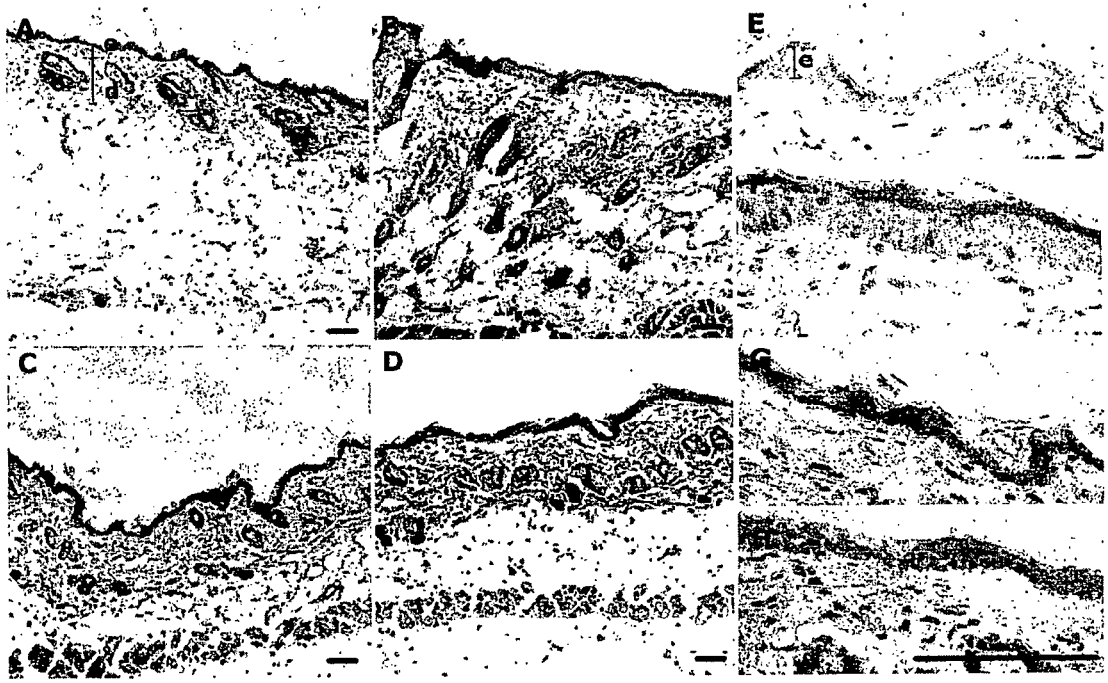

FIG. 20 shows the results of microscopic observation for the skin tissue of TPA-treated wild-type mice and EC SOD-overexpressed mice A, E: the skin tissue of acetone-treated wild-type mice;
B, F: the skin tissue of TPA-treated wild-type mice;
C, G: the skin tissue of acetone-treated EC SOD-overexpressed mice;
D, H: the skin tissue of TPA-treated EC SOD-overexpressed mice;
e: epidermal layer; d: dermal layer;
size bar: 100 μm; magnification: A-D 100×, E-H 400×.

Figure 21A:
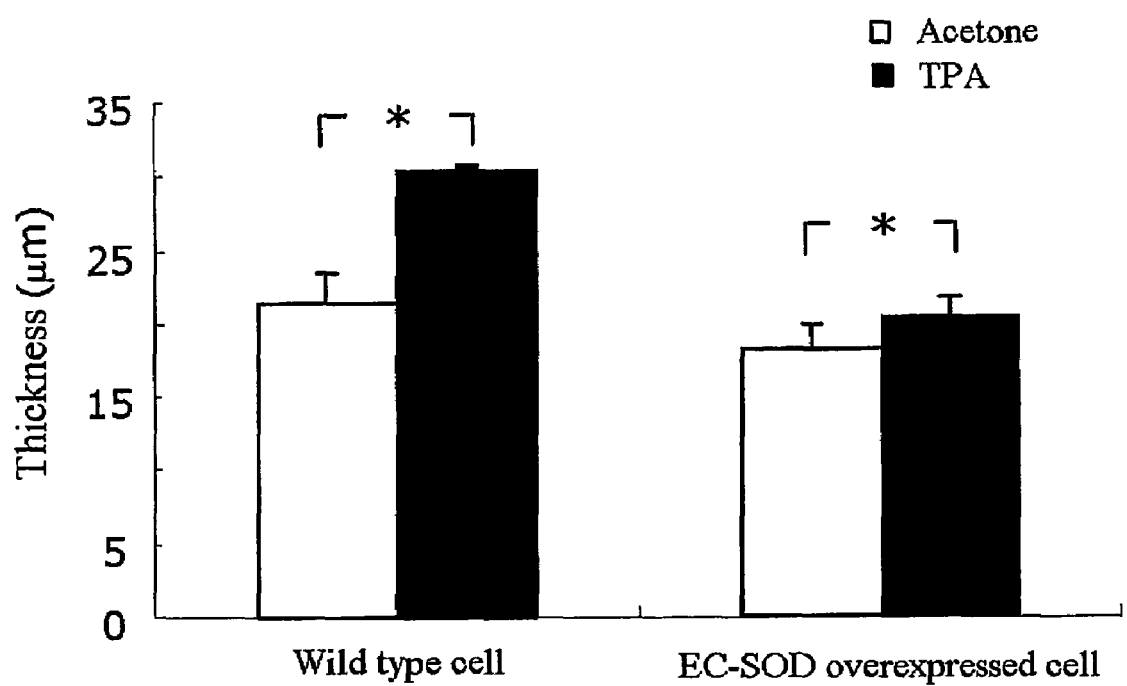

FIG. 21A is a graph showing the sum of epidermal thickness and dermal thickness of TPA-treated wild-type mice and EC SOD-overexpressed mice.

Figure 21B:
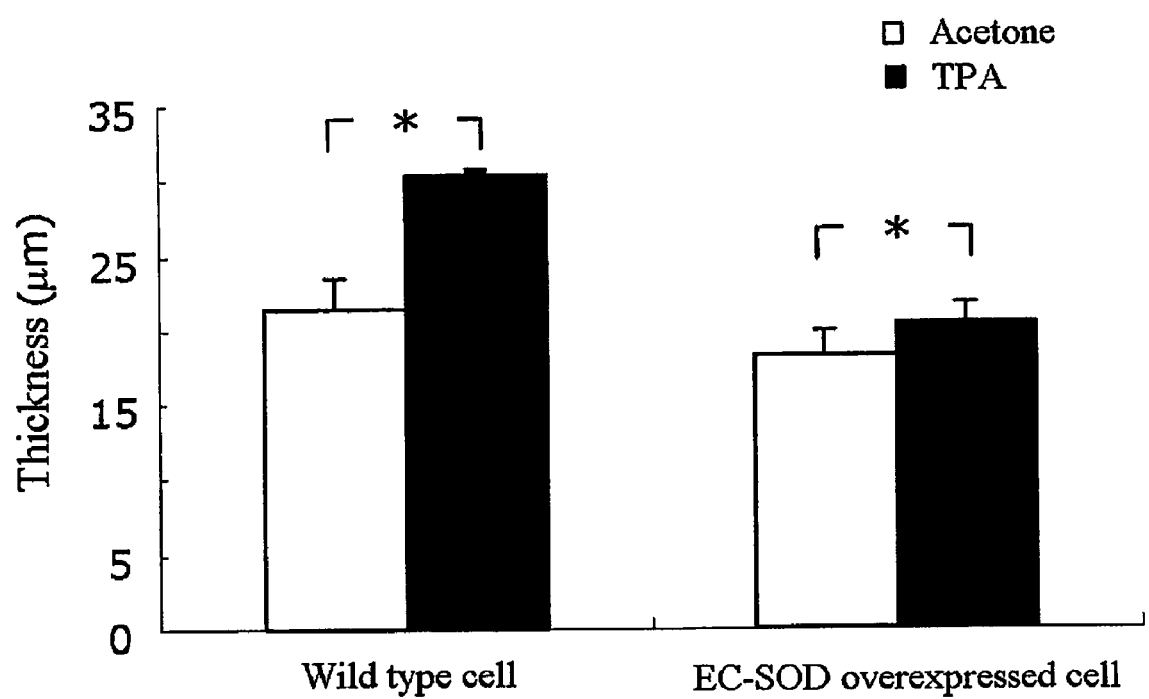

FIG. 21B is a graph showing the epidermal thickness of TPA-treated wild-type mice and EC SOD-overexpressed mice.

Figure 22:
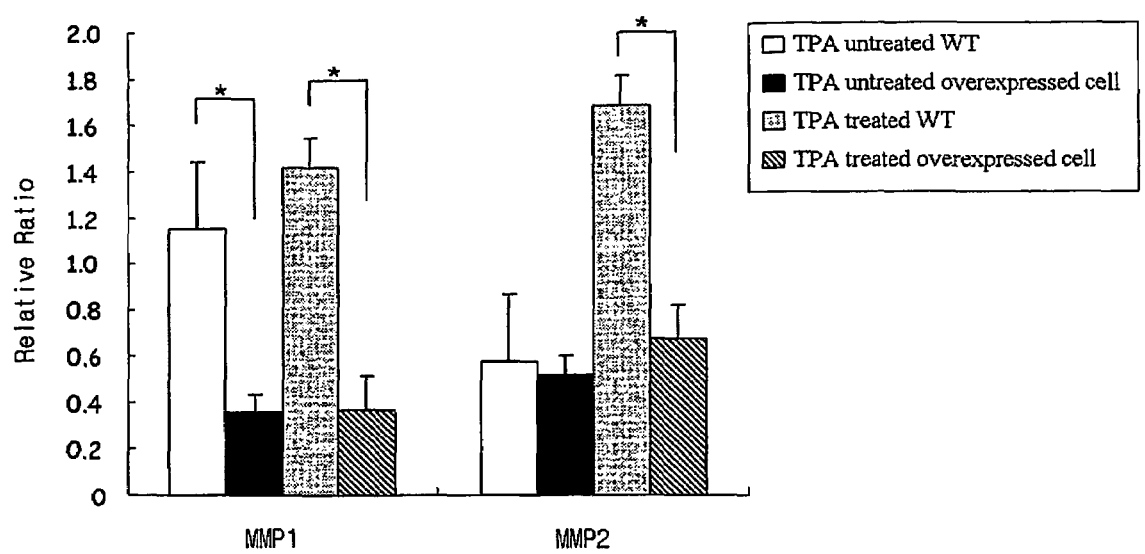

FIG. 22 shows the results of analysis for the expression of MMP1 and MMP2 in TPA-treated keratinocyte HaCaT cells and EC SOD-overexpressed HaCaT cells.

Figure 23A:
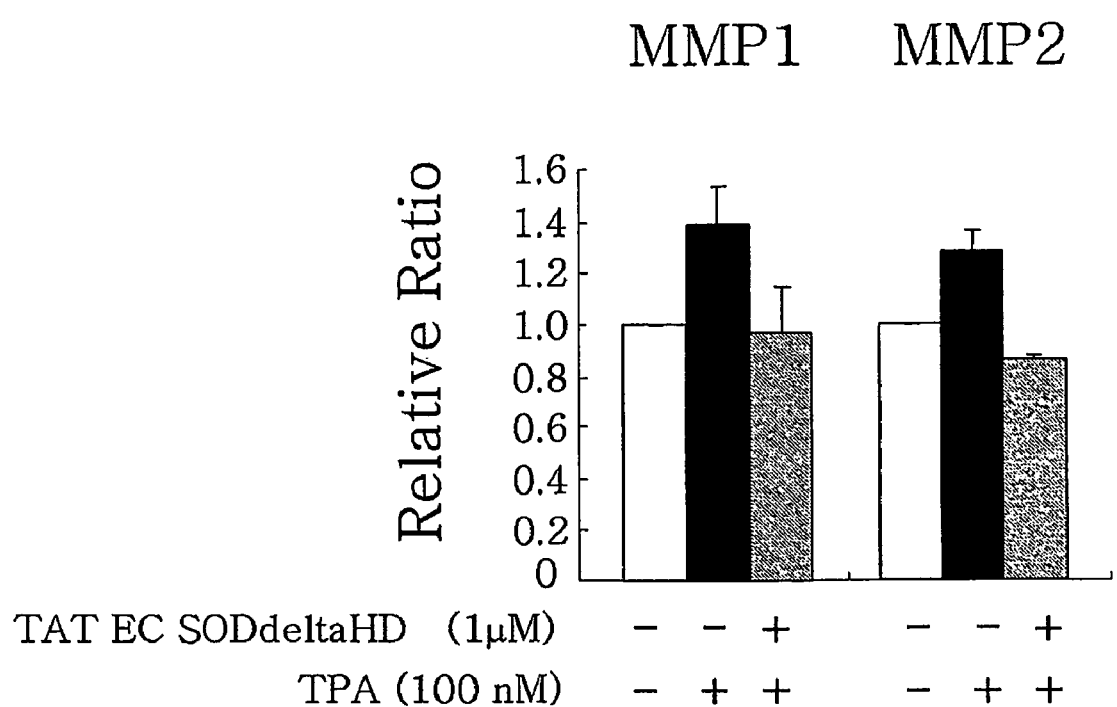

FIG. 23A shows the results of analysis for the expression of MMP1 and MMP2 in human fibroblasts according to treatment with a cell-transducing EC SOD fusion protein.

Figure 23B:
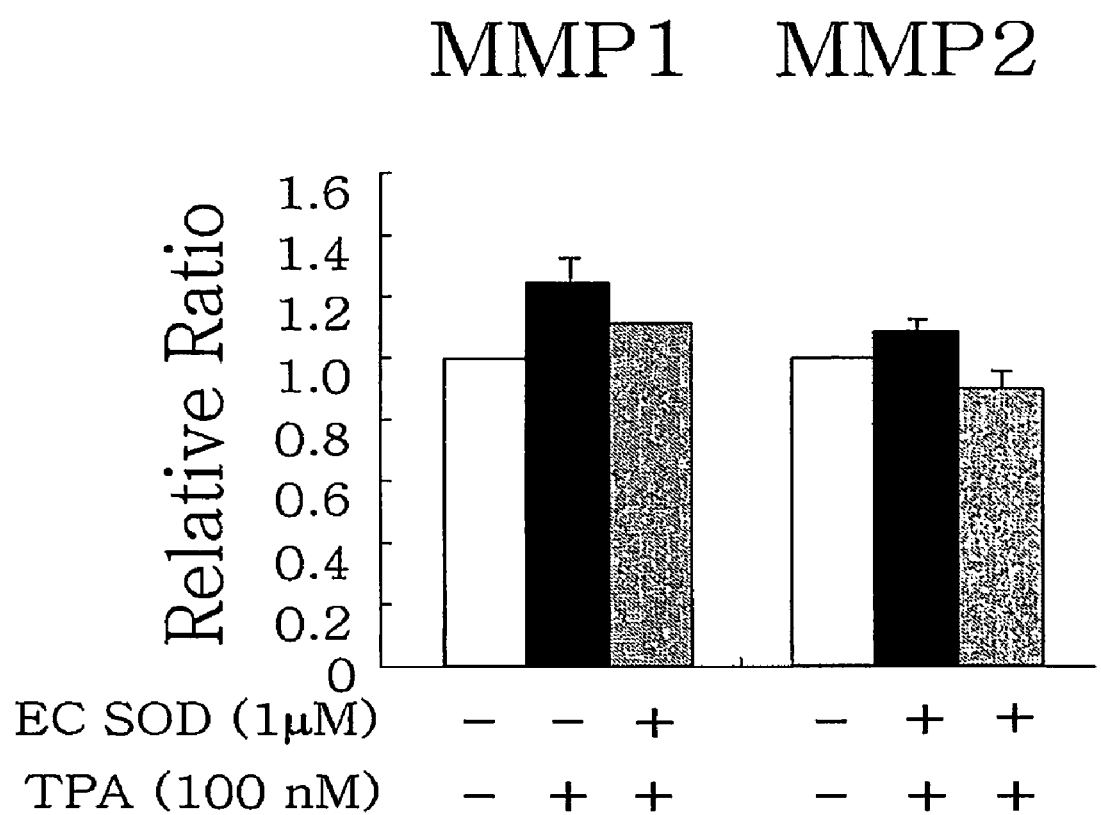

FIG. 23B shows the results of analysis for the expression of MMP1 and MMP2 in human fibroblasts according to treatment with an EC SOD protein.

BEST MODE FOR CARRYING OUT THE INVENTION

Hereinafter, the present invention will be described in detail by way of the following examples. It is to be understood, however, that these examples are given for illustrative purpose only and are not intended to limit the scope of the present invention.

Example 1

Examination of Distribution Pattern of EC SOD in Mouse Skin 1-1) Examination of Distribution Pattern of EC SOD in Mouse Skin Using Immunohistochemical Staining In order to examine the distribution of EC SOD in skin tissue, immunohistochemical staining was performed. The skin tissue taken from BALB/C mice (8 to 10-week-old, female, obtained from KRIBB, Taejon, Korea) was fixed in 4% paraformaldehyde and prepared into a paraffin block by a known method. The paraffin block was treated with xylene to remove paraffin, and dehydrated by treatment with alcohol. To enhance an immune response, the tissue sample was then thermally treated in citric acid buffer at 121° C. for 10 minutes. Next, the tissue sample was treated with 3% hydrogen peroxide ($H_2O_2$) to inhibit peroxidase, and reacted with a rabbit anti-mouse EC SOD antibody (primary antibody) diluted 1:500, for 60 minutes. The rabbit anti-mouse EC. SOD antibody was obtained by injecting mouse EC SOD into rabbits to immunize the rabbits. The tissue sample reacted with the antibody was washed with 0.1 M PBS and reacted with 200 μl of a biotin-conjugated goat anti-rabbit IgG-containing antibody (Universal LSAB 2 kit, Dako, Glostrup, Denmark) for 15 minutes. Also, pre-immune rabbit serum was used as a negative control group. After completion of the reaction, the tissue sample was washed with PBS, reacted with peroxidase-conjugated streptavidin, and color-developed with 3-amino-9-ethyl-carbazole (AEC, chromogen, Utah, USA), a substrate solution. The developed tissue sample was prepared into a test sample by a conventional method and observed under a microscope at a magnification of 400×.

Figure 1:
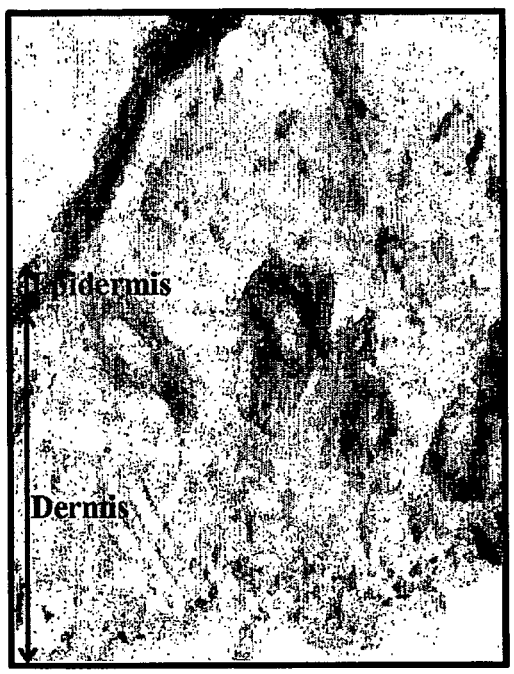
FIG. 1 is a photograph showing the results of immunohistochemical examination for the distribution pattern of EC SOD in mouse skin tissue.
Figure 1:
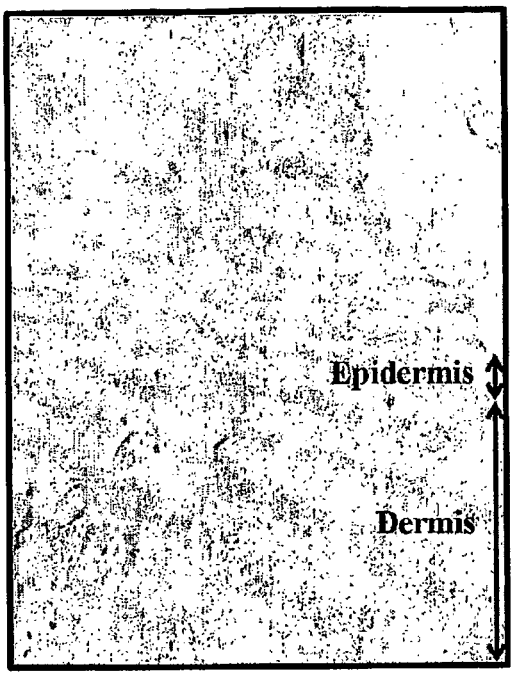

The test results revealed that EC SOD was distributed throughout the skin tissue. It was observed that EC SOD was widely distributed in the connective tissue of the dermal layer, and particularly, it was more strongly stained around the hair follicles and blood vessels of the dermal layer. Also, EC SOD was strongly stained also in the cells of the epidermal layer, and thus, it was inferred that EC SOD of these region of skin would have the activity associated scavenging roles to reactive oxygen species (see FIG. 1).

1-2) Examination of Expression Pattern of EC SOD in Mouse Skin Using Northern Blot Analysis The ear skin tissue of BALB/C mice in Example 1-1) was separated by cutting with surgical scissors and rinsed with $Ca^{2+}$ and $Mg^{2+}$-free phosphate-buffered saline (pH 7.4). The skin tissue was floated with the dermis side down on 0.5% trypsin (Gibco, Invitrogen Corporation, California, U.S.A) in PBS at 37° C. for 50 minutes while the dermal layer faced downward. Then, the epidermal layer was separated from the dermal layer.

Total RNA was isolated from each of the separated epidermal and dermal layers. 20 μg of the extracted RNA was electorphoresed in formaldehyde-containing 1.2% agarose gels, and the mRNA on the gel was transferred to a nylon membrane, after which the RNA attached to the membrane was crosslinked by UV. A $^{32}$P-labeled cDNA probe of EC SOD was hybridized to the membrane at 65° C. The cDNA of EC SOD was prepared by PCR-amplification using the pCRII TOPO vector (provided from professor Suh J G, College of Medicine, Hallym University) (Suh J G et al., *Mol Cells*. 30; 7(2), 204-7, 1997) containing a mouse skin EC SOD cDNA as a template and the following primers. The PCR amplification reaction consisted of the following: one cycle at 94° C.; 30 cycles of 30 sec at 94° C., 30 sec at 55° C., and 45 sec at 72.5° C.; and one cycle of 5 min at 72.5° C.

```
Sense primer (SEQ ID NO: 1):
5'-ATG TTG GCC TTC TTG TTC-3'

Anti-sense primer (SEQ ID NO: 2):
5'-TTA AGT GGT CTT GCA CTC-3'
```

After completion of the hybridization, the membrane was washed and exposed to a film. The exposed film was developed to confirm mRNA, and analyzed with a molecular imager (Image Master-VDS, Phamacia Biotech). A significant difference between the test groups was assayed with Student's t-test.

The results showed that the expression of EC SOD mRNA was about 7 times stronger in the dermal layer than in the epidermal layer (see FIG. 2). From the test results, it could be inferred that EC SOD is strongly expressed in the fibroblasts and endothelial cells of the dermal layer. From such results, it was suggested that EC SOD would protect the skin, and particularly, it would have high activity of protecting the dermal connective tissue from reactive oxygen species.

1-3) Examination of Expression Pattern of EC SOD in Mouse Skin After Irradiation with UVA In order to directly examine the role of EC SOD in the in vivo skin, the dorsal skin of mice was irradiated with UVA, the total RNA was isolated from the dorsal skin of mice at different time points after UVA irradiation and subjected to Northern blot analysis to investigate the effect of UVA irradiation on the expression pattern of EC SOD.

The BALB/C mice were divided into each group of three animals. Theirs backs were shaved and after 24 hours, irradiated with different intensities of UVA. The mice were irradiated at an intensity of 5 $kJ/m^2$ and 25 $kJ/m^2$ radiated at an intensity of by means of 6 UVA lamps (F24T12/BL/HO, National Biological corporation USA) emitting 9.7 $mW/cm^2$, respectively. A control group was not irradiated with UVA.

The skin tissues were taken from UVA irradiated mice at indicated time points. From the separated skin tissue, total RNA was isolated and then subjected to Northern blot analysis in the same manner as in Example 1-2) to investigate the expression pattern of EC SOD mRNA. The amount of expressed mRNA was quantitatively analyzed using a molecular imager. As a loading control, GAPDH was used.

The results were showed as mean±standard deviation, and the expression level of each of the test groups was showed as a value relative to the expression level of the control group taken as 100%. Also, a significant difference between the control group and the test groups was assessed with Student's t-test.

As the result, the expression of EC SOD was not influenced by an UVA irradiation of 5 $kJ/m^2$. However, when the mice were irradiated with UVA of 25 $kJ/m^2$, the expression of EC SOD was initially reduced, and 6 hours after the UV irradiation, reached a maximum point of 338±7.2% ($p<0.05$), and then, 96 hours after the UV irradiation, showed a tendency to decrease (see FIG. 3). Thus, it could be found that the expression of EC SOD is controlled according to the intensity of UVA and the elapsed time after the UVA irradiation. From such results, it was inferred that EC SOD would perform a function of protecting the skin tissue from reactive oxygen species overproduced after UVA irradiation and changes caused thereby.

1-4) Examination of Expression Pattern of EC SOD in Mouse Skin After Irradiation with UVB The dorsal skin of mice was irradiated with UVB, and then, RNA was extracted from the irradiated skin at different time points and subjected to Northern blot analysis to investigate the effect of UVB irradiation on the expression pattern of EC SOD. According to the same method as described in Example 1-3), the BALB/C mice were divided into each groups of three animals, and then they were irradiated with 2 $kJ/m^2$, 8 $kJ/m^2$ and 15 $kJ/m^2$, respectively, by means of 6 UVB lamps (FS24T12/UVB/HO, National Biological corporation, USA) emitting 0.6 $mW/cm^2$. After the UV irradiation, the expression pattern of mRNA was examined in the same manner as in Example 1-2).

As the result, when the mice were irradiated with 2 $kJ/m^2$ of UVB, the expression of EC SOD mRNA was initially reduced to 73±3% ($p<0.05$), but after 24 hours, restored to the level of the control group. When the mice were irradiated with 8 $kJ/m^2$ of UVB, the expression of EC SOD was increased to 212±11% ($p<0.05$) after 48 hours. In the case of the irradiation at an intensity of 15 $kJ/m^2$, the expression level of EC SOD was increased to 322±15% ($p<0.05$) after 48 hours, which is the highest value (see FIG. 4). Accordingly, it could be found that the expression of EC SOD is influenced by the intensity of UVB and the elapsed time after UV irradiation.

1-5) Examination of Expression Pattern of EC SOD in Mouse Skin After Treatment with PUVA Mice were treated with PUVA which is widely used in clinical treatment. Then, RNA was isolated from the treated mice at the different time points and subjected to Northern blot analysis to investigate the effect of PUVA treatment on the expression pattern of EC SOD.

According to the same method as described in Example 1-3), two test groups each consisting of three BALB/C mice were applied with 100 µl of 8-MOP (0.2% (w/v) 8-methoxy psolaren, ICN Pharmaceuticals, Costa Mesa, USA) on their dorsal skin, and after one hour, irradiated with UVA at intensities of 5 kJ/m$^2$ and 25 kJ/m$^2$, respectively, by means of the same UV lamps as used in Example 1-3). At this time, a control group was treated only with 0.2% (w/v) 8-MOP. After the UV irradiation, the expression pattern of EC SOD mRNA was examined in the same manner as in Example 1-2).

As the result, in the case of the control group treated with 8-MOP only and in the case of the test group treated with 8-MOP followed by irradiation with 5 kJ/m$^2$ of UVA, there was no change in the expression level of EC SOD mRNA. In the case of the test group irradiated with 25 kJ/m$^2$ of UVA, the expression level of EC SOD mRNA was increased slowly after the UV irradiation and reached 264±4.5% (p<0.05) after 48 hours, indicating that the expression level of EC SOD was remarkably increased.

From the above test results, it could be found that the expression pattern of EC SOD is influenced by the intensity of UV and the elapsed time after UV irradiation. Accordingly, it was inferred that EC SOD would have an association with the activity of protecting the skin from toxic reactive oxygen species produced either after UV irradiation or in an inflammatory reaction caused by UV.

Example 2

Change in Reactive Oxygen in Mouse EC SOD-Overexpressed Cell Line According to UV Irradiation EC SOD was overexpressed in mouse embryonic fibroblasts using a Tet off-MEF/3T3 inducible gene expression system (Clontech), a known gene expression system, after which the cells were irradiated with UV and measured for intracellular reactive oxygen.

2-1) Construction of Mouse EC SOD-Overexpressed Cell Line

Mouse EC SOD cDNA was inserted into the Sal I site of a TRE2 vector (Clontech), a control vector of a TET OFF system. The mouse EC SOD was prepared by PCR-amplification using pCRII TOPO vector (provided from professor Suh, J G, College of Medicine, Hallym University) containing mouse EC SOD cDNA as a template with the following primers. The PCR amplification reaction consisted of the following: one cycle at 94° C.; 30 cycles of 30 sec at 94° C., 30 sec at 55° C., and 45 sec at 72.5° C.; and one cycle of 5 min at 72.5° C.

```
Sense primer (SEQ ID NO: 3):
5'-AGT CTC GAG ATG TTG GCC TTC TTG TTC TAC GGC-3'

Anti-sense primer (SEQ ID NO: 4)
5'-GATC CTC GAG TGG TCT TGC ACT CGC TCT-3'
```

The prepared vector and a hygromycin-resistant sequence-containing pTG76 plasmid (University of Geneva Medical School, Geneva, Switzerland) were introduced into mouse embryonic fibroblasts (Clontech), a MEF3T3/TET OFF cell line, using lipofectin (Invitrogen). Then, the cells were cultured in a medium containing 100 µg/mL hygromycin, and only resistant colonies were selected. Of the colonies, a cell line overexpressing the EC SOD upon the removal of tetracycline was constructed. Namely, the colonies were cultured in a DMEM medium containing 10% TET-free FBS (Clontech), L-glutamine, 5000 UI/L penicillin streptomycin, 100 µg/mL G418, 100 µg/mL hygromycin and 2 ng/mL tetracycline and then tetracycline was removed in order to overexpress EC SOD. The removal of tetracycline was performed by culturing the cells in a fresh medium free of tetracycline. The cells were cultured in the fresh medium for 48 hours so as to induce the overexpression of EC SOD and measured for the expression level and activity of EC SOD. The expression level of EC SOD was measured by Northern blot analysis in the same manner as in Example 1-2), and the activity of EC SOD was analyzed by adding 20 µl of the medium sample and 10 µl of xanthine oxidase (SIGMA) to 3 ml of 50 mM sodium carbonate buffer (containing 0.1 mM cytochrome C, and 0.5 mM xanthine, pH 10.0) and then measuring the absorbance at 550 nm.

In the result, when tetracycline was removed, the expression and activity of EC SOD mRNA showed a tendency to increase with the passage of time. Thus, a cell line overexpressing the mouse EC SOD could be constructed.

2-2) Measurement of Reactive Oxygen in Mouse EC SOD-Overexpressed Cell Line After UV Irradiation The mouse EC SOD-overexpressed cell line constructed in Example 2-1) was irradiated with UV and then measured for the amount of reactive oxygen. Before the UV irradiation, the media were removed and the mouse EC SOD-overexpressed cell was washed two times with PBS (pH 7.4), and irradiated with UV in the presence of PBS. The UV irradiation was performed by irradiating the cell line with 10 J/cm$^2$ of UVA by means of an UVA lamp emitting 27 mW/cm$^2$, and irradiating the cell line with 20 mJ/cm$^2$ of UVB by means of three UVB lamps emitting 1.15 mW/cm$^2$. The PUVA treatment was performed by treating the cell line with 0.1% 8-MOP and, after 30 minutes, washing the treated cell line with PBS two times and irradiating with 2 J/cm$^2$ of UVA.

After irradiating the cells with UV as described above, the cells were sampled at different time points and reacted with 10 µM HE (dihydroethyidium) at 37° C. for 20 minutes. The resulting sample was washed with PBS containing 1% (w/v) BSA and 0.1% (w/v) NaN$_3$ and was analyzed with a flow cytometer. A value measured with the flow cytometer was showed as a value relative to the reactive oxygen species amount of the control group taken as 1. As the control group, a cell line which has not been irradiated with UV was used.

The results showed that, when the mouse EC SOD-overexpressed cell line was irradiated with 10 J/cm$^2$ of UVA, the amount of reactive oxygen species was reduced continuously for 6 hours after the UV irradiation (see FIG. 7A). Also, when the EC SOD-overexpressed cell line was irradiated with 20 mJ/cm$^2$ of UVB, the concentration of reactive oxygen species was about 60% reduced one hour after the UV irradiation as compared to the control cell line (see FIG. 7B). Also, when the EC SOD-overexpresed cell line was treated with PUVA, the amount of intracellular reactive oxygen was dramatically reduced as compared to the EC SOD-nonoverexpressed cell line (see FIG. 7C).

From the above results, it could be found that EC SOD not only functions in serum and extracellular matrices but also has the activity of effectively reducing the concentration of reactive oxygen species in cells.

Example 3

Effect of UV Irradiation on Cell Death in Human EC SOD-Overexpressed Cell Line 3-1) Construction of Human EC SOD-Overexpressed Cell Line In order to examine a change in reactive oxygen in a human EC SOD-overexpressed cell line according to UV irradiation, a human EC SOD-expressed cell line was constructed. For this purpose, human EC SOD cDNA was first inserted into the XbaI and EcoRI sites of pcDNA 3.1/myc-His(A) (Invitrogen). The human EC SOD cDNA was prepared by PCR-amplification using pUC18-hEC SOD vector (provided from professor Marklund, Clinical chemistry, Sweden) (Karin Hjalmarsson, *Proc Natl Acad Sci USA Vol.* 84, 6340-4, 1987) containing an human EC SOD cDNA as a template with the following primers. The PCR amplification reaction consisted of the following: one cycle of 4 min at 98° C.; 30 cycles of 30 sec at 98° C., 30 sec at 55° C., and 45 sec at 72° C.; and one cycle of 5 min of 72° C.

```
Sense primer (SEQ ID NO: 5):
5'-ATC TCT AGA ATG CTG GCG CTA CTG TGT-3'

Anti-sense primer (SEQ ID NO: 6)
5'-ATC GAA TCC TCA GGC GGC CTT GCA CTC GCT CTC-3'
```

The resulting PCR product was separated by agarose gel electrophoresis, treated with XbaI and EcoRI enzymes, and the resulting product inserted into a pcDNA 3.1/myc-His(A) vector (see FIG. 8). The resulting plasmid was transformed into HaCaT cells (provided from Professor N. E. Fusenig, The University of Heidelberg, Germany), a human keratinocyte cell line, using lipofectin (Invitrogen). Then, the transformed cells were cultured in a 500 μg/ml neomycin (Gibco)-containing media, and only resistant colonies were selected, thus constructing an EC SOD-overexpressed cell line.

In order to confirm the overexpression of EC SOD in the cells, Western blot analysis was performed. The EC SOD-overexpressed cell line was reacted with PBS containing 1% NP-40, 0.1% SDS and protease inhibitor, followed by centrifugation, and the supernatant was collected, thus extracting a protein from the EC SOD-overexpressed cell line. The extracted protein was subjected to 15% SDS-PAGE, moved to a nitrocellulose membrane, and blocked with 5% non-fat milk/TBS-0.1% Tween 20 solution for 1 hour. Thereafter, the resulting protein was reacted with a HIS antibody (Santa Cruz) diluted 200:1, for one hour, and washed three times with TBS-0.1% Tween 20 solution. Next, the reaction material was reacted with peroxidase-conjugated anti-rabbit IgG for 1 hour and washed three times, after which the expression of EC SOD was examined with an ECL kit (Amersham Bioscience). Also, a protein of a non-transformed HaCaT cell line was used as a negative control.

The results showed that, in the negative control HaCaT cell line, the histidine-bound EC SOD was not detected, but in the cell line transformed with the EC SOD cDNA-containing plasmid, the histidine-bound EC SOD was detected, thus indicating that EC SOD was overexpressed in the transformed cell line (see FIG. 9).

3-2) Measurement of Cell Death in Human EC SOD-Overexpressed Cell Line After UV Irradiation The human EC SOD-overexpressed cell line constructed in Example 3-1) was UV-irradiated and then measured for the amount of reactive oxygen species. Before the UV irradiation, the media were removed and human EC SOD-overexpressed cell line was washed twice with PBS (pH 7.4), and irradiated with UVB in the presence of PBS. The UV irradiation was performed by irradiating the cell line with each of 10, 20 and 30 mJ/cm$^2$ of UVB by means of three UVB lamps emitting 1.15 mW/cm$^2$. After 24 hours, cells were sampled, washed with PBS (pH 7.4), and fixed in 80% ethanol. The cells were precipitated by centrifugation, washed with PBS (pH 7.4), suspended in 1 ml PBS (pH 7.4), and reacted with 4 ml of permeabilization solution (0.5% Tripton X-100, 200 μg/ml RNase A, 10 μg/ml propidium iodide) for 15 minutes. Cell cycle analysis was performed with a flow cytometer, and apoptototic cells (Sub G1) were showed as percentage. At this time, a HaCaT cell line which has not been transformed was used as a negative control group.

In the result, when UVB was irradiated at an intensity of 10 mJ/cm$^2$, the percentage of apoptototic cells did not show a great difference between the control group cell line and the EC SOD-overexpressed cell line. However, when UVB was irradiated at intensities of 20 and 30 mJ/cm$^2$, the percentage of apoptototic cells was significantly lower in the EC SOD-overexpressed cell line than in the control group (see FIG. 10).

From the above results, it could be found that the overexpression of EC SOD can reduce cell death caused by UV in the human keratinocyte cell line. This suggests that the overexpression of EC SOD can protect skin cells from UV damages.

Example 4

Preparation of Cell-Transducing Human EC SOD Fusion Protein 4-1) Preparation of TAT-EC SOD Fusion Protein, R9-EC SOD Fusion Protein and K10-EC SOD Fusion Protein Expression Vectors Fusion proteins where a human EC SOD protein had been fused to protein transduction domains, a HIV-1 Tat (RKKRRQRRR), an oligopeptide consisting of 9 arginine residues, and an oligopeptide consisting of 10 lysine residues respectively, were prepared. Also, a fusion protein where a ΔHD/EC SOD protein deleted a heparin domain from the EC SOD had been fused to HIV-1 Tat was prepared.

For this purpose, human EC SOD and ΔHD/EC SOD cDNAs were first prepared. The human EC SOD c DNA was prepared by PCR-amplification using pUC18-hEC SOD vector (provided from professor Marklund, Clinical chemistry, Sweden) containing a human EC SOD cDNA as a template and the following primers (SEQ ID NO: 7 and SEQ ID NO: 8). The PCR amplification reaction consisted of the following: one cycle of 4 min at 98° C.; 30 cycles of 30 sec at 98° C., 30 sec at 55° C., and 45 sec at 72° C.; and one cycle of 5 min at 72° C.

```
Sense primer (SEQ ID NO: 7):
5'-GAT CCT CGA GTG GAC GGG CGA GGA CTC GGC-3'

Anti-sense primer (SEQ ID NO: 8):
5'-GAT CCT CGA GTC AGG CGG CCT TGC ACT CGC T-3'
```

In the case of the ΔHD/EC SOD deleted a heparin domain from the EC SOD, PCR amplification was performed under the same conditions as described above except that the following primers (SEQ ID NO: 9 and SEQ ID NO: 10) were used.

```
Sense primer (SEQ ID NO: 9):
5'-GAT CCT CGA GTG GAC GGG CGA GGA CTC GGC-3'

Anti-sense primer (SEQ ID NO: 10)
5'-AAT GCT CGA GTC ACT CTG AGT GCT CCC GCG C-3'
```

The resulting PCR products were separated by agarose gel electrophoresis and treated with XhoI enzyme. Each of the enzyme-treated mature EC SOD cDNA and mature ΔHD/EC SOD cDNA was inserted into the XhoI site of a pET15(b)-

TAT vector (provided from professor Choi SY, Department of Genetic Engineering, Hallym University) containing the fundamental domain of HIV-1 Tat (amino acid residues 49-57: RKKRRQRRR) (Park et al., *J Gen Virol*, 83:1173-1181, 2002), thus preparing the respective expression vectors. Also, the enzyme-treated mature EC SOD cDNA was inserted into the XhoI site of each of a pET15(b)-R9 vector (provided from professor Choi SY, Department of Genetic Engineering, Hallym University) containing an oligopeptide consisting of 9 arginine residues (Ryu et al., *Mol Cells*, 16:385-391, 2003) and a pET15(b)-K10 vector (provided from professor Choi S Y, Department of Genetic Engineering, Hallym University) containing an oligopeptide consiting of 10 lysine residues, thus preparing the respective expression vectors (see FIG. 11).

4-2) Transformation of *E. coli* and Expression of Fusion Protein

*E. coli* BL21 (DE3) (Novagen) was transformed with each of the expression vectors prepared in Example 4-1) by a heat shock method. Then, the transformed *E. coli* strain was inoculated in 250 ml of an ampicillin-containing LB medium and cultured at 37° C. to an $A_{600}$ of 0.8 while stirring at 200 rpm. The culture solution was added with IPTG (1 mM) and further cultured so as to induce the overexpression of the EC SOD fusion protein.

4-3) Purification of Fusion Proteins

The cells cultured in Example 4-2) were collected by centrifugation, suspended in binding buffer (5 mM imidazole, 0.5 M NaCl, 20 mM Tris-HCl, 6 M urea, pH 7.9), and disrupted by sonication. Since each of the fusion proteins contains 6 histidines at the N-terminal end, it can be purified with a very high purity of about 90% by immobilized metal-chelate affinity chromatography. For this reason, the cell disruption solution was centrifuged, and the collected supernatant was immediately loaded into a 2.5 ml $Ni^{2+}$-nitrilotriacetic acid sepharose column and washed with a ten-fold volume of binding buffer and a six-fold volume of washing buffer (30 mM imidazole, 0.5 M NaCl, 20 mM Tris-HCl, (pH 7.9)), after which the fusion protein was eluted with elution buffer (1 M imidazole, 0.5 M NaCl, 20 mM Tris-HCl, (pH 7.9)). Next, fractions containing each of the fusion proteins were collected and desalted by performing Sephadex G-25 column (PD 10 column, Amersham Biotech) chromatography. The purified TAT-EC SOD fusion protein, TAT-ΔHD/EC SOD fusion protein, K10-EC SOD fusion protein and R9-EC SOD fusion protein were identified by electrophoresis (see FIGS. 12 and 13). The amino acid sequences and base sequences of the TAT-EC SOD fusion protein, the TAT-ΔHD/EC SOD fusion protein, the K10-EC SOD fusion protein and the R9-EC SOD fusion protein are as shown in SEQ ID NO: 12 to SEQ ID NO: 19.

4-4) Examination of Cell-Transduction Ability of Fusion Proteins

The cell-transduction ability of the inventive TAT-EC SOD fusion protein, TAT-ΔHD/EC SOD fusion protein, K10-EC SOD fusion protein and R9-EC SOD fusion protein was examined using a human keratinocyte cell line. Namely, HaCaT cells were seeded onto a slide chamber, and after 24 hours, treated with the EC SOD fusion proteins prepared according to the present invention, at concentrations of each of 0, 1, 2 and 4 μM. After 3 hours, the resulting substance was fixed in 3.7% formaldehyde/PBS (pH 7.4) for 10 minutes and incubated with 0.1% triton X-100/PBS for 10 minutes to make them permeable. Then, it was blocked with 2% (v/v) FCS/PBS at ambient temperature for one hour, reacted with HIS antibody/2% FCS/PBS/PBS (Santacruz, USA) diluted 100:1, for 1 hour, and washed three times with 2% FBS/PBS. The resulting substance was reacted with FITC-conjugated IgG (Serotec) diluted 50:1, for 1 hour. The reaction substance was reacted with 1 μg/ml PI for 15 minutes and washed three times with 2% FBP/PBS. Then, it was mounted and observed with a confocal microscopy. As a negative control group, an EC SOD protein which has not been fused with the protein transduction domain was used.

Also, from the HaCaT cells treated with the TAT-EC SOD fusion protein or the TAT-ΔHD/EC SOD fusion protein, a protein was extracted and subjected to Western blot analysis using the HIS antibody. The intensity of the analyzed bands was quantified and showed as percentage relative to the control group EC SOD protein to which the transduction domain has not been fused. Furthermore, the cell penetration efficiencies of the K10-EC SOD fusion protein and the R9-EC SOD fusion protein were analyzed by Western blot analysis and showed as percentage relative to the cell transduction efficiency of the TAT-EC SOD fusion protein.

The results showed that the negative control group could not penetrate into the cells, whereas the TAT-EC SOD fusion protein effectively transduced into the cells so that it was located within the cytoplasm. Also, the TAT-ΔHD/EC SOD fusion protein transduced into the cells so that it was located within the cytoplasm (see FIG. 14).

Moreover, the results of calculation of cell penetration rate showed that the cell transduction efficiencies of the TAT-EC SOD fusion protein and the TAT-ΔHD/EC SOD fusion protein were increased with an increase by concentration dependent manner with the fusion protein, and the cell transduction efficiency of the TAT-EC SOD fusion protein was higher than that of the TAT-ΔHD/EC SOD fusion protein (see FIG. 15).

Also, the R9-hEC SOD fusion protein where an oligopeptide consisting of 9 arginine residues has been fused to EC SOD showed the highest transduction efficiency. Next to the R9-hEC SOD fusion protein, the cell transduction efficiency was higher in the order of the K10-hEC SOD fusion protein having an oligopeptide consisting of 10 lysine residues fused to hEC SOD, and the TAT-EC SOD fusion protein (see Table 1).

TABLE 1

| Cell transduction efficiency of EC SOD fusion protein | |
|---|---|
| EC SOD fusion protein | transduction efficiency (%) |
| TAT-hEC SOD | 100 |
| R9-hEC SOD | 160 |
| K10-hEC SOD | 150 |

4-5) Preparation of PEP-1-EC SOD Fusion Protein

A fusion protein having a protein transduction domain PEP-1 peptide (KETWWETWWTEWSQPKKKRKV) fused to a human EC SOD protein was prepared. Also, a fusion protein where a ΔHD/EC SOD having a deletion of a heparin domain in the EC SOD has been fused to a PEP-1 peptide was prepared.

For this purpose, the TAT-EC SOD expression vector or TAT-ΔHD/EC SOD expression vector prepared in Example 4-1) was cut with the NdeI-XhoI restriction enzyme, into which a PEP-1 peptide was then inserted, thus preparing PEP1-EC SOD and PEP1-ΔHD/EC SOD expression vectors. A double-strand oligonucleotide which had been artificially made of the following primer set was ligated to each of the expression vectors (see FIG. 16).

```
Sense primer (SEQ ID NO: 20):
5'-TATGAAAGAAACCTGGTGGGAAACCTGGTGGACCGAATGGTC
TCAGCCGAAAAAAAAAACGTAAAGTG C-3'

Anti-sense primer (SEQ ID NO: 21):
5'-TCGABCACTTTACGTTTTTTTTCGGCTGAGACCATTCGGTCCA
CCAGGTTTCCCACCAGGTTTCTTTCC-3'
```

The prepared expression vectors were expressed and purified in the same manner as in Examples 4-2) and 4-3). The amino acid sequences and base sequences of the PEP-1-EC SOD fusion protein and the PEP-1-ΔHD/EC SOD fusion protein are as shown in SEQ ID NO: 22 to SEQ ID NO: 25.

4-6) Examination of Cell-Transduction Ability of PEP-1-EC SOD Fusion Protein

The cell-transduction ability of the inventive PEP-1-EC SOD fusion protein purified in Example 4-5) was examined using a HeLa cell line (provided from professor Soo Young Choi, Department of Genetic Engineering, Hallym University), a human breast cancer cell line. Namely, the HeLa cells were seeded onto a slide chamber, and after 24 hours, treated with 1 μM of each of the inventive PEP-1-EC SOD fusion protein and an EC SOD protein as a negative control group. After one hour, the cells were fixed in 3.7% formaldehyde/PBS (pH 7.4) at room temperature for 10 minutes, and reacted with 0.1% Triton X-100/PBS for 10 minutes so as to make them permeable. The cells were blocked with 2% (v/v) FCS/PBS at room temperature for one hour, and reacted with HIS antibody/2% FCS/PBS/PBS (Santacruz, USA) diluted 400:1, for 1 hour, followed by washing three times with 2% FBS/PBS. Then, the cells were treated with Cy3-conjugated rabbit IgG (Molecular Probe Co) diluted 100:1, for one hour, followed by washing three times with 2% FBP/PBS. The reaction substances were mounted and observed with a fluorescent microscope. As the negative control group, an EC SOD protein to which the protein transduction domain has not been fused was used.

The results showed that the negative control group did not transduce into the cells (see A of FIG. 17), whereas the PEP-1-EC SOD fusion protein transduced into the cells so that it was located within the cytoplasm (see B of FIG. 17).

Example 5

Therapeutic Effect of EC SOD and Cell-Transducing EC SOD Fusion Protein in Skin Disease Models with TPA 5-1) Examination of Expression of EC SOD in Skin Tissue of TPA-Treated Wild-Type Mice and EC SOD-Overexpressed Mice Wild-type mice and EC SOD-overexpressed mice were treated with TPA, and the expression pattern of EC SOD in the skin tissue of the mice was examined by immunohistochemical staining.

For this purpose, EC SOD-overexpressed transgenic mice were constructed. As test animals, hybrid mice ((C57BL/6×CBA)F1) purchased from KRIBB, Korea, were used. To induce superovulation, 5 IU of PMSG (pregnant mare's serum gonadotropin) and 5 IU of hCG (human chronic gonadotropin) were injected into the abdominal cavity of female mice at an interval of 48 hours, and then mated with male mice of the same family line at 1:1. Next day morning, the presence or absence of a vaginal plug was observed, and only an individual with the vaginal plug was butchered from which an oviduct was taken. From the oviduct ampulla, embryos were collected. As culture medium, 0.4% BSA-containing M16 culture medium was used.

In order to make mice where the skin tissue-overexpression of EC SOD had been induced, the mouse EC SOD cDNA of the mouse EC SOD cDNA-containing pCRII TOPO vector as described in Example 2-1) was cut with a restriction enzyme and inserted into a pBS KS vector containing a human keratin K14 promoter. Also, the vector was inserted with chicken ovalbumin poly (A) to induce the effective expression in vitro. In order to inject DNA into the embryos, the expression vector was cut with restriction enzymes Hind and XhoI (FIG. 18). The restriction enzyme-cut DNA was electrophoresed on 1% agarose gel, recovered by dialysis, and isolated and purified with phenol-chloroform. It was dialyzed in 10 mM Tris (pH 7.4)/0.2 mM EDTA) to a final concentration of 4 ng/μl. The foreign gene-containing DNA solution was injected into the pronuclei of one-cell-stage embryos. The foreign gene-injected embryos were cultured to the two-cell stage, and cultured healthy embryos were selected. Female ICR mice in heat were mated with male mice, and next day, the presence or absence of a vaginal plug was observed, and a mouse with the vaginal plug was used as a surrogate mother. About 15-20 embryos well grown to the two-cell stage were collected and transplanted into the oviduct ampulla of the pseudopregnant recipients, after which a muscular layer and an epidermal layer were sutured to each other. After the transplantation, born animals were grown for about 3 weeks. Next, their tail was cut about 1 cm, treated with lysis buffer at 55° C. and extracted genomic DNA with phenol. The genomic DNA was PCR-amplified with the following primer set so that whether it had been transformed or not was examined. The PCR amplification reaction consisted of the following: one cycle at 94° C.; 30 cycles of 30 sec at 94° C., 30 sec at 51° C., and 45 sec at 72.5° C.; and one cycle of 5 min at 72.5° C.

```
Sense primer (SEQ ID NO: 26):
5'-TTG TCT CTA ATA GAG GGT C-3'

Anti-sense primer (SEQ ID NO: 27):
5'-TCA AGC CTG TCT ATC TTC T-3'
```

The transgenic mice as described above and wild-type mice were treated with TPA by a known method, double TPA treatment (Zhaorigetu et al., *Oncology Rep* 10:537-534, 2003). At two days before the TPA treatment, the dorsal hairs of 10-week-old female mice were shaved with an electric razor for animals. Then, a solution of 8.1 nmol of TPA (Sigma Co., USA) in 200 μl of acetone was treated on the shaved skin tissue for two consecutive days, at interval of 24. For a control group, only 200 μl acetone was treated on the skin tissue in the same times. At one hour after the last TPA treatment, the skin tissue of the mice was separated and fixed in 4% paraformaldehyde, dehydrated with ethyl alcohol, and embedded in paraffin. After cutting the skin tissue with a microtome at an interval of 5 μm, the skin tissue sample was attached to slide glass. This tissue sample was treated with xylene to remove paraffin, dehydrated with ethyl alcohol, treated with 0.3% Triton X-100 to increase the penetrability of the solution, and treated with 3% $H_2O_2$ to inhibit peroxidase contained in the cells. Next, 10% goat serum was added to block the reaction and treated with an EC SOD polygonal antibody diluted 1:50. After completion of the reaction, the tissue was color-developed with a DAKO LSAB kit (peroxidase universal, DAKO Co.) by DAB (diaminobenzidine) reaction. The developed tissue sample was prepared into a sample by a conventional method and observed under a microscope at a magnification of 100×.

From the results, it could be found that, when the wild-type mice were treated with TPA, EC SOD would be expressed throughout the skin tissue of the treated mice. Also in case of the transgenic mice, EC SOD was expressed throughout the skin tissue. Particularly in the case of the transgenic mice, it was observed that EC SOD was strongly expressed in the epidermal and follicular tissues, indicating that EC SOD was overexpressed in the skin tissue of the transgenic animals as compared to the wild type mice (FIG. 19).

5-2) Observation and Thickness Measurement of Skin Tissue of Wild-Type Mice and EC SOD-Overexpressed Mice Treated with TPA According to the same method as described in Example 5-1), wild-type mice and EC SOD-overexpressed mice were treated with TPA and, after one hour, the mouse skin tissue was separated, fixed, dehydrated with ethyl alcohol, and embedded in paraffin. Then, it was cut with a microtome at an interval of 5 µm, and the skin tissue sample was attached to slide glass. The tissue sample was treated with xylene to remove paraffin, dehydrated with ethyl alcohol, stained with hematoxylin and eosin, mounted, and observed with a microscope.

Also, various randomly selected areas of each of the wild-type mice and EC SOD-overexpressed mice treated with TPA and the control group mice treated with acetone were imaged with an image capture system, after which the sum of thickness of epidermis and dermis, and the thickness of only epidermis, were measured with a rule.

The results showed that the epidermal thickness and dermal thickness of the wild-type mice treated with TPA were increased than those of the wild-type mice treated only with acetone without TPA treatment. Also, in the transgenic mice treated with TPA, the abnormal outgrowth of epidermis was observed as compared to the control group transgenic mice but was very negligible (FIG. 20).

It could be found that the sum of epidermal thickness and dermal thickness and only the epidermal thickness in the wild-type mice treated with TPA were 2.1 times and 1.4 times increased, respectively, than those of the control group mice treated with acetone, indicating there was a definite difference between the wild-type mice and the control group mice (FIG. 21A). On the other hand, the sum of epidermal thickness and dermal thickness and only the epidermal thickness in the EC SOD-overexpressed mice treated with TPA were 1.1 times increased than those of the control group mice treated with acetone, indicating there was a slight difference between the wild-type mice and the control group mice (FIG. 21B).

From the above test results, it could be found that a change in the thickness of the skin tissue caused by TPA can be inhibited by EC SOD. Accordingly, EC SOD can be used for the treatment of chronic inflammatory skin diseases characterized by the growth of epithelium, particularly epidermal hyperplasia.

5-3) Change in Expression of MMP in EC SOD-Expressed Cells Treated with TPA

Human keratinocyte HaCaT cells into which the human EC SOD overexpression vector had been introduced were treated with TPA, and the expression of MMP in the cells was analyzed by RT-PCR.

For this purpose, the HaCaT cells into which the human EC SOD overexpression vector of example 3-1) had been introduced were treated with 100 nM TPA. After the TPA treatment, the cells were cultured for 1 hour at 37° C., and the total RNA of the cultured cells was extracted using trizol solution (GibcoBRL). 10 µg of the total RNA, as a template, was subjected to reverse transcription with a reverse transcription system (Promega Co.) so as to obtain cDNA. The cDNA was PCR-amplified with a primer set shown in Table 2 below, and the amplified DNA was developed on 1.5% (w/v) agarose gel (containing 0.002% ethidium bromide) for 15 minutes. The amplification of the DNA was observed under UV, after which the intensity of the amplified DNA band was measured. GAPDH was used as an internal control group, and the measured intensity of the DNA band was showed as a value relative to the intensity of GAPDH taken as 1.0.

TABLE 2

Primers used in RT-PCR for analysis of MMP expression

| Primer | Sequence | SEQ ID NO |
|---|---|---|
| Human MMP1 sense primer | 5'-ATCTACAGCTCCTTTGGTCTT-3' | 28 |
| Human MMP1 anti-sense primer | 5'-ATCTACAGCTCCTTTGGCTT-3' | 29 |
| Human MMP2 sense primer | 5'-AACCCTCAGAGCCACCCCTA-3' | 30 |
| Human MMP2 anti-sense primer | 5'-GTGCATACAAAGCAAACTGC-3' | 31 |
| GAPDH sense primer | 5'-CATCTTCCAGGAGCGAGACC-3' | 32 |
| GAPDH anti-sense primer | 5'-TCCACCACCCTGTTGCTGTA-3' | 33 |

The results showed that the expression of MMP1 in the EC SOD-overexpressed HaCaT cells without TPA treatment was reduced as compared to the wild-type HaCaT cells. Meanwhile, the expression of MMP1 in the wild-type cells one hour after the TPA treatment was remarkably increased, but the expression of MMP1 in the EC SOD-overexpressed cells was the same level as that of without TPA treatment.

A group of without TPA treatment, the expression of MMP2 was slightly lower in the EC SOD-overexpressed cells than in the wild-type cells. After the TPA treatment, the expression of MMP2 in the wild-type cells was remarkably increased, but in the EC SOD-overexpressed cells, it was similar to that before the TPA treatment (FIG. 22).

The above results suggest that EC SOD can inhibit the expression of MMP by TPA, thus inhibiting sking aging.

5-4) Change in Expression of MMP in Human Fibroblasts According to Treatment with Human EC SOD Protein and Cell-Transducing EC SOD Fusion Protein It is known that MMPs which control the change of extracellualr matrices in tissue are mostly expressed in human fibroblasts. For this reason, human fibroblasts were treated with each of the EC SOD protein and the cell-transducing EC SOD fusion protein, and a change in the expression of MMP according to the treatment was examined.

Human fibroblasts were treated with 1 μM of each of the human EC SOD protein and the purified TAT-ΔHD/EC SOD fusion protein prepared in Example 4-3) and then with 100 nM TPA, and cultured at 37° C. for 1 hour. The cells were collected, and the expression levels of MMP1 and MMP2 were measured by performing RT-PCR in the same manner as in Example 5-3). A control group was not treated with TPA. The intensity of DNA band of each test group treated with TPA was expressed as a value relative to the DNA band strength of the control group taken as 1.0.

The human EC SOD protein was prepared by transforming E. coli with the human EC SOD expression vector prepared in Example 3-1) and expressing and purifying the vector in E. coli in the same manners as in Example 4-2) and Example 4-3).

The results showed that when the human fibroblasts were treated with TPA, the expression of MMP1 and MMP2 was increased. On the other hand, when the human fibroblasts were treated with either the TAT-ΔHD/EC SOD fusion protein or the EC SOD protein and then with TPA, the expression of MMP1 and MMP2 was inhibited (FIGS. 23A and 23B).

From the above results, it could be found that the TAT-ΔHD/EC SOD fusion protein or the EC SOD protein has the activity of inhibiting the expression of MPP enzymes induced by TPA, and the activity can be further increased by imparting cell-transduction ability to the EC SOD protein.

Example 6

Inhibition of Degranulation of Mast Cells According to Treatment with EC SOD Protein Mast cells were treated with the inventive EC SOD protein, and the inhibition of degranulation of the mast cells according to the protein treatment was examined. For this purpose, bone marrow cells collected from BALB/C mice were cultured in 50% nutrient medium (RPMI 1640 containing 100 unit/ml penicillin, 100 mg/ml streptomycin, 10 mg/ml gentamicin, 2 mM L-glutamine, 0.1 mM non-essential amino acids, 10% bovine fetal serum) and 50% WEHI-3 cell preservation medium for at least 3 weeks so as to obtain BMMC (bone marrow-derived mast cells) which are more than 95% homogeneous. 1×10$^6$ cells/ml of the BMMCs were added with 1 μg/ml or 10 μg/ml of the human EC SOD protein and cultured for 30 minutes. The culture solution was reacted with KL/LPS/IL-1β for 30 minutes, and the culture supernatant and the cell lysate were collected. 25 μl of each of the supernatant and the cell lysate were reacted with p-nitrophenyl-2-acetamido-2-dioxy-b-D-glucopyranoside (Sigma Co. USA) as a substrate. The reaction material was added with 0.2 M glycine-NaOH (pH 10.7) to stop the reaction, and measured for enzyme activity using a spectrophotometer at 410 nm to examine the inhibition of release of β-hexosamidase. Also, a control group was treated with PBS. The inhibition of enzyme activity (%) was showed as percentage relative to the release of β-hexosamidase in the PBS-treated control group taken as 100%.

Inhibition of enzyme activity (%)=(release of β-hexosamidase in EC SOD-treated test group/release of β-hexosamidase in PBS-treated control group)×100

In the results, the BMMC test groups treated with 1 μg/ml or 10 μg/ml of EC SOD showed enzyme activity inhibitions of 9.87% and 11.97%, respectively, relative to the control group (Table 3). Thus, it could be found that EC SOD has the effect of inhibiting the degranulation of mast cells so that it can treat allergic skin diseases such as atopy.

TABLE 3

Inhibition of degranulation of mast cells according to treatment with EC SOD protein

| | A405[a] | Release of β-hexosamidase | Enzyme activity Inhibition (%) |
|---|---|---|---|
| Control group (treated with PBS) | 0.111 ± 0.010 | 18.38 | 100 |
| EC SOD  10 μg/ml | 0.100 ± 0.008 | 16.57 | 9.87 |
|  1 μg/ml | 0.098 ± 0.009 | 16.18 | 11.97 |
| Total β-hexosamidase activity | 0.606 ± 0.077 | 100 | — |

[a]n = 3, mean ± standard deviation

INDUSTRIAL APPLICABILITY

As described above, the EC SOD protein according to the present invention is distributed throughout the skin tissue while it has the effects of removing reactive oxygen species in skin cells and inhibiting the overgrowth of epidermal cells, the expression of MMP and the degranulation of mast cells. Thus, the inventive EC SOD protein will be useful for the prevention and treatment of skin diseases. Also, the cell-transducing EC SOD fusion protein prepared by fusing the protein transduction domain to EC SOD has excellent cell-transduction ability so that it will be useful for preventing and treating skin diseases.

What is claimed is:

1. A method for treating skin diseases, which comprises administering to a subject in need thereof an effective amount of an isolated EC SOD protein or an expression vector comprising a polynucleotide encoding the EC SOD protein, wherein the EC SOD protein comprises an amino acid sequence of SEQ ID NO: 11, wherein the skin diseases are selected from the group consisting of skin cancer, pigmentation disease, photoaging, atopy, urticaria and allergy.

* * * * *